(12) United States Patent
Alexander et al.

(10) Patent No.: US 10,945,589 B2
(45) Date of Patent: Mar. 16, 2021

(54) FLEXIBLE ENDOSCOPIC PERIPHERAL

(71) Applicant: TREBLE INNOVATIONS, LLC, Springville, UT (US)

(72) Inventors: Ian Joseph Alexander, Boerne, TX (US); Brian Dean Owens, Plano, TX (US); Roland Clifford Park, Springville, UT (US)

(73) Assignee: TREBLE INNOVATIONS, LLC, Springville, UT (US)

( * ) Notice: Subject to any disclaimer, the term of this patent is extended or adjusted under 35 U.S.C. 154(b) by 45 days.

(21) Appl. No.: 16/043,449

(22) Filed: Jul. 24, 2018

(65) Prior Publication Data

US 2018/0326189 A1 Nov. 15, 2018

Related U.S. Application Data

(63) Continuation of application No. 13/654,409, filed on Oct. 17, 2012, now Pat. No. 10,029,079.
(Continued)

(51) Int. Cl.
*A61B 1/00* (2006.01)
*A61B 1/005* (2006.01)
(Continued)

(52) U.S. Cl.
CPC ........ *A61B 1/00108* (2013.01); *A61B 1/0002* (2013.01); *A61B 1/005* (2013.01);
(Continued)

(58) Field of Classification Search
None
See application file for complete search history.

(56) References Cited

U.S. PATENT DOCUMENTS 4,545,369 A 10/1985 Sato
4,604,993 A 8/1986 Moriwaki et al.
(Continued)

FOREIGN PATENT DOCUMENTS

JP 2005046273 A 2/2005
WO 2011013733 A1 2/2011

OTHER PUBLICATIONS

"CellScope Launches iPhone Device for Diagnosing Ear Infections", http://block.launch.co/blog/cellscope-launches-iphone-device-for-diagnosing-ear-infectio.html [retrieved from the Internet on May 28, 2013], 5 pages.
(Continued)

*Primary Examiner* — Aaron B Fairchild
(74) *Attorney, Agent, or Firm* — Goodhue, Coleman & Owens, P.C.

(57) ABSTRACT

An endoscopic peripheral includes a first end of a flexible cable including at least a camera and one or more lights enclosed by a tip at the first end. The tip is tapered for insertion of a portion of the first end into a body of a patient. The endoscopic peripheral includes one or more controls interconnected with and controlling the camera and the one or more lights. A second end of the flexible cable terminates in a plug configured to physically connect the endoscopic peripheral to an electronic device. The electronic device powers the camera and the one or more lights and displays content captured by the camera. The endoscopic peripheral is plug and play when connected to the electronic device. The diameter of the diameter of the endoscopic peripheral between the first end and the second end is approximately the same.

24 Claims, 13 Drawing Sheets

Related U.S. Application Data

(60) Provisional application No. 61/595,885, filed on Feb. 7, 2012, provisional application No. 61/585,658, filed on Jan. 12, 2012, provisional application No. 61/559,190, filed on Nov. 14, 2011, provisional application No. 61/548,596, filed on Oct. 18, 2011.

(51) Int. Cl.

| | | |
|---|---|---|
| *A61B 1/05* | (2006.01) | |
| *A61B 1/06* | (2006.01) | |
| A61M 29/00 | (2006.01) | |
| A61B 1/04 | (2006.01) | |
| A61M 29/02 | (2006.01) | |
| A61M 25/10 | (2013.01) | |
| A61M 25/06 | (2006.01) | |
| A61B 1/233 | (2006.01) | |

(52) U.S. Cl.
CPC ........ *A61B 1/0014* (2013.01); *A61B 1/00016* (2013.01); *A61B 1/00018* (2013.01); *A61B 1/00101* (2013.01); *A61B 1/00114* (2013.01); *A61B 1/00135* (2013.01); *A61B 1/00142* (2013.01); *A61B 1/00154* (2013.01); *A61B 1/05* (2013.01); *A61B 1/0676* (2013.01); *A61B 1/00032* (2013.01); *A61B 1/0051* (2013.01); *A61B 1/00052* (2013.01); *A61B 1/00066* (2013.01); *A61B 1/00133* (2013.01); *A61B 1/04* (2013.01); *A61B 1/233* (2013.01); *A61M 25/0662* (2013.01); *A61M 25/10* (2013.01); *A61M 25/1018* (2013.01); *A61M 25/1025* (2013.01); *A61M 29/00* (2013.01); *A61M 29/02* (2013.01); *A61M 2025/1043* (2013.01)

(56) References Cited

U.S. PATENT DOCUMENTS

| | | |
|---|---|---|
| 4,862,874 A | 9/1989 | Kellner |
| 4,879,991 A | 11/1989 | Ogiu |
| 5,025,778 A | 6/1991 | Silverstein et al. |
| 5,117,818 A | 6/1992 | Palfy |
| 5,257,617 A | 11/1993 | Takahashi |
| 5,318,008 A | 6/1994 | Bullard |
| 5,599,301 A | 2/1997 | Jacobs et al. |
| 5,601,594 A | 2/1997 | Best |
| 5,879,289 A | 3/1999 | Yarush et al. |
| 5,941,818 A | 8/1999 | Hori et al. |
| 5,951,461 A | 9/1999 | Nyo et al. |
| 6,086,528 A | 7/2000 | Adair |
| 6,091,453 A | 7/2000 | Coan et al. |
| 6,106,457 A | 8/2000 | Perkins et al. |
| 6,165,123 A | 12/2000 | Thompson |
| 6,402,687 B1 | 6/2002 | Ouchi |
| 6,405,729 B1 | 6/2002 | Thornton |
| 6,432,046 B1 | 8/2002 | Yarush et al. |
| 6,692,431 B2 | 2/2004 | Kazakevich |
| 6,750,971 B2 | 6/2004 | Overbeck et al. |
| 7,559,892 B2 | 7/2009 | Adler et al. |
| 7,879,061 B2 | 2/2011 | Keith et al. |
| 8,088,101 B2 | 1/2012 | Chang et al. |
| 2001/0041825 A1 | 11/2001 | Shibata et al. |
| 2002/0022763 A1 | 2/2002 | Sano et al. |
| 2002/0051080 A1* | 5/2002 | Tanaka ............... H04N 5/23206 348/552 |
| 2002/0068851 A1 | 6/2002 | Gravenstein et al. |
| 2003/0040685 A1 | 2/2003 | Lewkowicz et al. |
| 2003/0130564 A1 | 7/2003 | Marione et al. |
| 2004/0024334 A1 | 2/2004 | Boncompte |
| 2004/0027459 A1 | 2/2004 | Segawa et al. |
| 2004/0092825 A1 | 5/2004 | Madar et al. |
| 2004/0133089 A1 | 7/2004 | Kilcoyne et al. |
| 2004/0186351 A1 | 9/2004 | Imaizumi et al. |
| 2005/0049462 A1 | 3/2005 | Kanazawa |
| 2005/0075538 A1 | 4/2005 | Banik et al. |
| 2005/0171418 A1 | 8/2005 | Lin |
| 2005/0177024 A1 | 8/2005 | MacKin |
| 2005/0228224 A1 | 10/2005 | Okada et al. |
| 2006/0137690 A1 | 6/2006 | Gunaratnam et al. |
| 2006/0161045 A1 | 7/2006 | Merril et al. |
| 2006/0183971 A1 | 8/2006 | Haviv |
| 2006/0206005 A1 | 9/2006 | Ou-Yang et al. |
| 2006/0235458 A1 | 10/2006 | Belson |
| 2006/0272640 A1 | 12/2006 | Abullon |
| 2007/0142703 A1 | 6/2007 | Lu |
| 2007/0161853 A1 | 7/2007 | Yagi et al. |
| 2007/0162095 A1 | 7/2007 | Kimmel et al. |
| 2007/0185377 A1 | 8/2007 | Murakami et al. |
| 2007/0219600 A1 | 9/2007 | Gertner et al. |
| 2007/0276183 A1 | 11/2007 | Melder |
| 2008/0021273 A1 | 1/2008 | MacKin |
| 2008/0081947 A1 | 4/2008 | Irion et al. |
| 2008/0103521 A1 | 5/2008 | Makower et al. |
| 2008/0139881 A1 | 6/2008 | Cover et al. |
| 2008/0139884 A1 | 6/2008 | Myers |
| 2008/0232131 A1 | 9/2008 | Suda |
| 2008/0275483 A1 | 11/2008 | Makower et al. |
| 2008/0312499 A1 | 12/2008 | Handa et al. |
| 2009/0076330 A1 | 3/2009 | Ashida |
| 2009/0095303 A1 | 4/2009 | Sher et al. |
| 2009/0187071 A1 | 7/2009 | Kim |
| 2009/0188507 A1 | 7/2009 | LaCava |
| 2009/0194109 A1 | 8/2009 | Doshi et al. |
| 2009/0247828 A1 | 10/2009 | Watanabe et al. |
| 2009/0253967 A1 | 10/2009 | Gill et al. |
| 2010/0016673 A1 | 1/2010 | Bandy et al. |
| 2010/0030031 A1 | 2/2010 | Goldfarb et al. |
| 2010/0063358 A1 | 3/2010 | Kessler |
| 2010/0095969 A1 | 4/2010 | Schwartz et al. |
| 2010/0099946 A1 | 4/2010 | Jenkins et al. |
| 2010/0100181 A1 | 4/2010 | Makower et al. |
| 2010/0101580 A1 | 4/2010 | Stumm et al. |
| 2010/0145146 A1 | 6/2010 | Melder |
| 2010/0210901 A1 | 8/2010 | Makower et al. |
| 2011/0018988 A1 | 1/2011 | Kazakevich et al. |
| 2011/0137290 A1 | 6/2011 | Flickinger et al. |
| 2011/0261183 A1 | 10/2011 | Ma et al. |
| 2012/0071824 A1 | 3/2012 | Chang et al. |
| 2013/0204085 A1 | 8/2013 | Alexander et al. |

OTHER PUBLICATIONS

Aliexpress "Witson New WiFi iPad iPhone Android supported borescope, 9.8mm camera with 2 Leds, Support iPad/Phone/Android surveilance", http://www.aliexpress.com/store/product/WITSON-NEW-WIFI-iPad-iPhone-aNDROID-SUPP... [retrieved from the Internet on May 2, 2013], 12 pages.

Euroclinic Medial Equipment, Diagnostic & Imaging. "EVS ED400 Camera System", http:www.euroclinic.it/en/product-php?p=78&d=3, retrieved from the Internet on May 2, 2013], 2 pages.

Sanostec, Inc., Sinus Cones vs. Max-Air Nose Cones, Retrieved Nov. 15, 2011 from http://www.maxaimosecones.com/sinus-cones-vs-max-air-nose-cones-products/.gclid=CLrys4--3wsCFYxb7AodiXezQA.

SweetVision Imaging, innovative endoscope imaging systems, http:sweetvision-imaging.com [retrieved from the Internet on May 2, 2013], 10 pages.

* cited by examiner

FLEXIBLE ENDOSCOPIC PERIPHERAL

RELATED APPLICATIONS

This application claims priority to U.S. provisional patent application Ser. No. 61/548,596 entitled "Nasal Guide and Method of Use Thereof", filed Oct. 18, 2011, U.S. provisional patent application Ser. No. 61/559,190 entitled "Portable Endoscope and Method of Use Thereof", filed Nov. 14, 2011, U.S. provisional patent application Ser. No. 61/585,658 entitled "Endoscopic Sheath and Method of Use Thereof", filed Jan. 12, 2012, and U.S. provisional patent application Ser. No. 61/595,885 entitled "Systems and Methods for Controlling Balloon Catheters" filed Feb. 7, 2012, and issued U.S. Pat. No. 10,029,079 Ser. No. 13/654,409 entitled "Endoscopic Peripheral" filed Oct. 17, 2012 the entire contents of which are all hereby incorporated by reference in their entirety. This application is related to U.S. utility patent application Ser. No. 13/654,401 entitled "Systems and Methods for Controlling Balloon Catheters", filed Oct. 17, 2012, the entire contents of which are all hereby incorporated by reference in their entirety.

BACKGROUND

Each year more and more surgical procedures are performed through the body orifices or surgically created openings. Procedures and surgeries within the body of the patient require positioning the necessary equipment, such as endoscopes. Endoscopy refers to looking inside and typically refers to looking inside the body for medical reasons using an endoscope, an instrument used to examine the interior portion of a body, such as a hollow organ or cavity of the body.

Some endoscopic procedures may require multiple medical professionals to ensure proper guidance and placement of the equipment due to the size, bulk, and awkwardness of the equipment. For example, many endoscopes may include handles, scopes, external processing equipment, and custom displays. The endoscopes may be extremely expensive preventing many medical professionals from purchasing or using endoscopes despite the many advantages offered. In many ways, current systems, devices, and techniques for performing endoscopic procedures fail to adequately address these and other issues.

SUMMARY

One embodiment of an endoscopic peripheral includes a first end of a flexible cable including at least a camera and one or more lights enclosed by a tip at the first end. The tip is tapered for insertion of a portion of the first end into a body of a patient. The endoscopic peripheral includes one or more controls interconnected with and controlling the camera and the one or more lights. A second end of the flexible cable terminates in a plug configured to physically connect the endoscopic peripheral to an electronic device. The electronic device powers the camera and the one or more lights and displays content captured by the camera. The endoscopic peripheral is plug and play when connected to the electronic device. The diameter of the diameter of the endoscopic peripheral between the first end and the second end is approximately the same.

Another embodiment of an endoscopic peripheral provides a first end including at least a camera and one or more lights. The endoscopic peripheral may also include a second end, which may include a plug to physically connect the endoscopic peripheral to a computing device or a wireless device. The endoscopic peripheral may also include a flexible cable for communicating content captured by the camera to the computing device or wireless device.

Another embodiment provides an endoscopic peripheral. The endoscopic peripheral may include a flexible cable having a first end. The first end may include at least a camera and one or more lights. The flexible cable may further have a second end. The second end may include a plug to physically connect the endoscopic peripheral to at least one of a computing device or a wireless device. The flexible cable may be adapted to communicate content captured by the camera to the computing device or wireless device.

Another embodiment provides an endoscopic peripheral. The endoscopic peripheral may include a first end including a camera and one or more lights at a tip. The first end may be flexible to be positioned for utilization. The endoscopic peripheral may include a second end including a plug for electrically connecting the endoscopic peripheral to an electronic device configured to display content captured by the camera. The endoscopic peripheral may also include a flexible cable connecting the first end and the second end.

Another embodiment provides a method for utilizing an endoscopic peripheral. The endoscopic peripheral may be physically connected to an electronic device. The electronic device powers at least a camera and one or more lights of the endoscopic peripheral. The endoscopic peripheral is interfaced with the electronic device to display the content captured by the camera.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION OF THE DRAWINGS

Figure 1A:
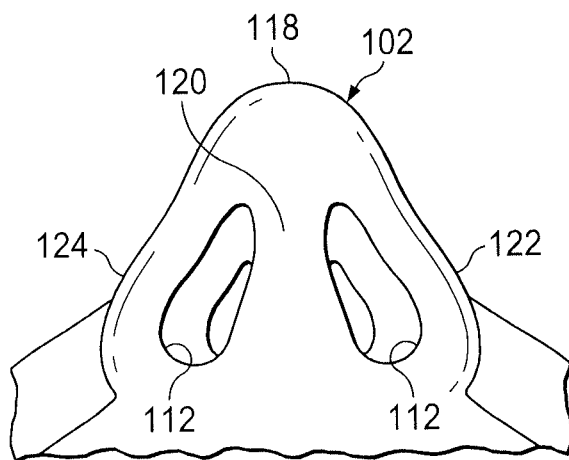
FIGS. 1A-C are pictorial representations of nose and nostril shapes in accordance with illustrative embodiments.

Illustrative embodiments provide an endoscopic peripheral. The endoscopic peripheral may be configured to communicate directly with a computing or communications device. The computing device may be a personal computer, laptop, desktop computer, or other data processing system or device. The communications device may be a wireless device, such as a cell phone, electronic book, mp3 player, media system, gaming system, PDA, tablet, iPhone, iPad, appliance, or so forth. The endoscopic peripheral may be utilized to capture video, images, and content in any number of spectrums, wavelength, and so forth.

In an illustrative embodiment, the endoscopic peripheral is small, portable, light weight, inexpensive and able to be utilized with existing electronic devices available to a medical professional. As a result, many patients that have not previously benefited from endoscopic analysis and treatment may receive the associated medical examination, analysis, and treatment.

In one embodiment, the endoscopic peripheral is a plug-and-play device or wireless device equivalent that may be utilized without specialized software or other components. A plug-and-play device provides a standard for the connection of peripherals, such that the endoscopic peripheral only needs to be connected to a computer or computing device in order to function as desired without additional requirements. For example, the default or installed software of the computing or communications device may be utilized to both view content, save the content, and otherwise manage the content. The computing or communications device may not need specific drivers, software, or other applications. As a result, the user may utilize the endoscopic peripheral with any number of commonly available electronic devices that have an electronic display and in any number of locations and circumstances.

In another embodiment, the endoscopic peripheral may be utilized with specialized logic or software for capturing, saving and sharing the content with any number of other users, such as doctors, nurses, dentists, physicians assistants, coworkers, or so forth. The software may be included in an operating system, program, set of instructions, or mobile application. For example, video or images captured by the endoscopic peripheral may be communicated to, transferred or shared with a medical professional, system, or networked device based on a request from the medical professional, an association with an identifier of the endoscopic peripheral, or in response to a request from the user. For example, a MAC address, IP address, website, dedicated server, IMEI, or other identifier may be utilized to send and receive content captured by the endoscopic peripheral.

The endoscopic peripheral may be utilized for any number of medical examinations including examining the ears, throat, nose, mouth, internal organs and tissues, and other orifices or surgically created openings in the body. The endoscopic peripheral may also be utilized for construction, structural review, or in any other number of circumstances where a small camera may be required. The use of the peripheral endoscope may also include telemedicine wherein an individual may capture data and transfer the data collected to a physician or appropriate healthcare provider in order to diagnose issues.

In one embodiment, the endoscopic peripheral may be disposable for one time or field use. In another embodiment, the endoscopic peripheral may be configured for cleaning, sanitizing, or may include a disposable cover for utilization with a number of patients or uses.

Another embodiment provides a portable endoscope. In one embodiment, the portable endoscope is a wand-shaped endoscope that may be utilized alone or with the nasal guide. The portable endoscope has a reduced footprint and is self-contained to wirelessly transmit video or still-images ("images" or "content") to one or more computing devices, which may be wired or wireless devices. In another embodiment, the camera of the portable endoscope may communicate and be powered through a wire or cable with an externally-connected transmitter and battery. The portable endoscope decreases the size and complexity of endoscopic systems and equipment. In addition, the portable endoscope includes interchangeable parts including a camera, lights, processing or logic components, a transmitter or transceiver, and/or a battery that may be adapted for the patient, medical professional, or medical procedure. Both the portable endoscope and the described guide may be utilized for any sort of visualization within the body of a patient. The portable endoscope may be utilized in a wireless mode or wired mode (when physically connected to and powered by or charged by a computing or communications device). Unless otherwise indicated, as used herein, "or" does not require mutual exclusivity.

Another embodiment provides a nasal guide and a method for utilizing the nasal guide. In one embodiment, the nasal guide provides a guide for inserting one or more endoscopes, catheters, guides, or other pieces of equipment into the nose of a patient for surgery or examination. Unless otherwise indicated, as used herein, "or" does not require mutual exclusivity. In particular, the nasal guide directs the medical equipment into the nose of the patient toward the sinuses and stabilizes the equipment during insertion, utilization, and removal of the equipment. As a result, surgeries, such as balloon sinuplasty, may be performed by a single medical professional or fewer medical professionals while still maintaining instrument stability. The nasal guide may include one or more walled openings, lumens, ports, or through holes for inserting the medical equipment.

The nasal guide may be configured to be secured utilizing elastic, bands, clips, or adhesives that may be adjusted or customized for each individual patient. For example, an elastic band may include a clip or strings for tightening or loosening the fit of the nasal guide in and against the nose of the patient. The nasal guide may be manufactured in a number of sizes and shapes to fit the noses (including snouts and muzzles) of patients of any age and size including humans and animals. In alternative embodiments, the guide may be configured for a mouth, ear(s), rectum, or other natural or surgically-created opening. The nasal guide gently expands the nostrils of the patient allowing the equipment and medical professional to more easily access an interior portion of the body or nose including the sinus cavity and sinuses. The opening action of the nasal guide may also help the patient breath before, during, or after the medical procedure is performed.

In one embodiment, the nasal guide may be configured to both receive and guide medical instruments deeper into the nose while expanding the nostrils and stabilizing the medical instruments during the procedure. As a result, fewer medical professionals may be required, and medical procedures may be performed with less concern about damaging the nostrils of the patient. The nasal guide may be configured for use in a single nostril or in both nostrils for enhanced stability. In addition, suction or oxygen attachments may be integrated with or attached to the nasal guide (portions inserted within the nose as well as external to the nose) allowing suction or oxygen to be applied to the patient through the nasal guide.

Any of the components and features of the illustrative embodiments, including the priority applications and related applications, may be combined in a nearly unlimited number of configurations best suited to fit the body of the patient and/or the needs of medical professionals.

Figure 1B:
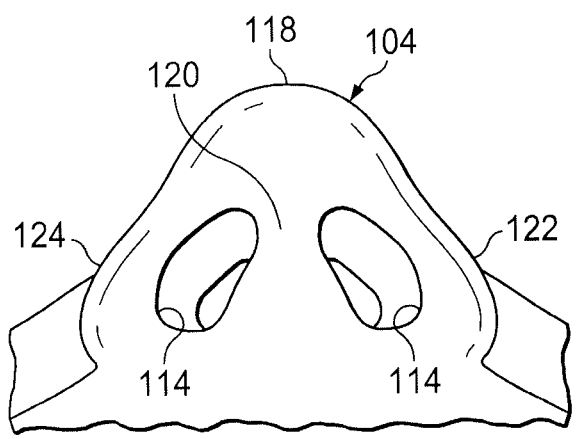
Figure 1C:
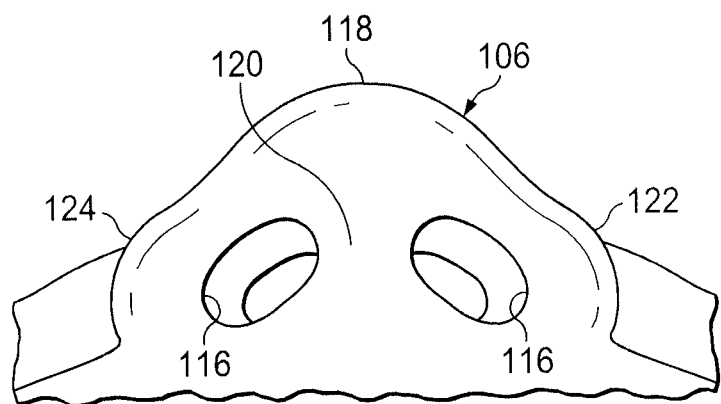

FIGS. 1A, 1B, and 1C are pictorial representations of various noses 102, 104, and 106 and nostril shapes with which the illustrative embodiments may be implemented. The visible part of the nose is the protruding part of the face that bears the nostrils or anterior nares. Typically, the shape of the nose is determined by the ethmoid bone and the nasal septum. The nasal septum separates the left and right airways of the nose to divide the two nostrils, and is formed mostly of cartilage. Nose and nostril sizes, shapes, and configurations vary by age, sex, race, and other factors. In addition, accidents, birth defects, and other factors may influence the size and shape of all interior and exterior portions of the nose, and such circumstances may be accounted for by the illustrative embodiments.

The nostrils 112, 114, and 116 vary between the different noses 102, 104, and 106. As shown for nose 102, the nose 102 includes a tip 118, columella 120, left lateral side 122, and right lateral side 124. The nasal guides of the illustrative embodiments are sized and shaped to conform to any number of noses and nostrils despite the differences in size and shape. The nasal guides may be utilized to guard against abrasion or damage to the nostrils 112, 114, and 116, and the interior and exterior periphery of the nose about the nostrils 112, 114, and 116 including the columella 120.

In one embodiment of the nasal guide, and use thereof, the patient may be distracted by the sensation of the portion of the nasal guide that fits into the patient's nostril(s) instead of focusing on the actual medical procedure that is being performed. As a result, scopes and other medical instruments may be more easily inserted and removed from the nostrils without damaging the soft interior and exterior skin and tissues of the nose.

In the illustrative embodiments, the term "patient" is utilized to refer to any individual, user, or animal that may have a medical procedure or other process performed through the nostrils of the nose, snout, or muzzle, or other natural or surgical opening of the body. Although the noses 102, 104, and 106 shown are human noses, the nasal guides may be sized and configured to be utilized for any patient, including any human, animal, or living creature. Non-limiting examples of animals on which the nasal guide may be used include domestic and exotic animals (i.e., mammals, reptiles, amphibians, marsupials, etc) of all sizes from cows and zebras to dogs and ferrets. The term "medical professional(s)" is utilized to refer to any doctor, professional assistant, nurse, dentist, veterinarian, remote operating system and device, clinician, forensic analyst, pathologist, diener, robot, or other person or electronic device that may perform a medical procedure or other process on a patient. It will be appreciated that operation of the nasal guide is not limited to medical professionals, as, in one embodiment, a user may self-administer or self-install the nasal guide, as well as any associated medical or other procedures.

Figure 2:
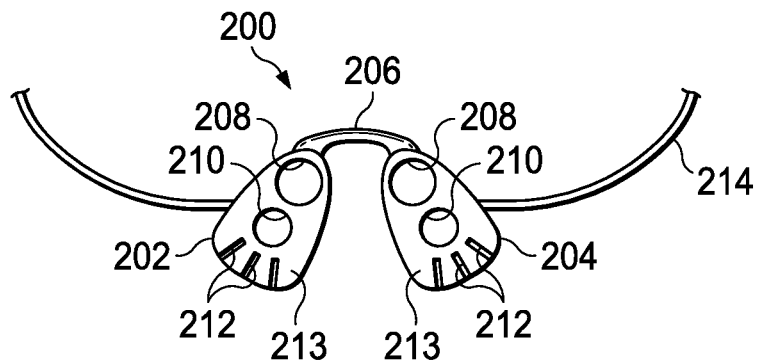
FIG. 2 is a schematic, plan view of a nasal guide in accordance with an illustrative embodiment.

FIG. 2 is a schematic, pictorial representation of a nasal guide 200 in accordance with an illustrative embodiment. The nasal guides of FIGS. 2-5 are shown from a plan view from which the nasal guides 200, 300, 400, 500 may be adjusted and fit into noses of any patients, such as the noses 102, 104, and 106 of FIGS. 1A, 1B, and 1C. The nasal guide 200 may include any number of components or elements as herein described. The potential size and shape of the nasal guide 200 are as varied as the patients that the nasal guide 200 may be used on, or the desired usage or specifications by which the nasal guide 200 is used.

The nasal guide 200 may alternatively be a guide for any body orifice or opening (e.g., ear, mouth, rectum, etc.), passageway, or tissue plane naturally or surgically created. For example, the guide may be adapted for use with an endoscope (such as the one subsequently described) for laparoscopic abdominal surgery, orthopedic procedures, robotic surgery, or intracranial or ear surgery. The nasal guide 200 may be used when numerous medical instruments are inserted into the body. The exterior portion (i.e., the portion of the guide adapted to be outside of the body) and the interior portion (i.e., the portion of the guide adapted to be inside of the body) of the guide may be configured for the surrounding entry site whether it be the ear or rectum of the patient, a surgically-created opening through the belly button of the patient, or other openings. For example, the exterior portion of the guide may be substantially flattened to be fit or flush to the patient. In addition, the guide may have only one side, or support, instead of two (e.g., the potential two-sided configuration of the nasal guide 200, shown in FIG. 2, may be for use in both nostrils).

In one illustrative embodiment, the nasal guide 200 is formed from hypoallergenic medical grade materials, such as U.S. Pharmacopeia (USP) Class V and VI silicon, rubber, polymers, or plastic materials (or a combination thereof), including those known in the art. In one embodiment, the nasal guide 200 is clear or transparent to provide the medical professional with maximum visibility of all covered and uncovered portions of the nose, whether exterior or interior to the nostrils. In one example, the nasal guide 200 may be molded from a single piece of medical grade plastic, silicon, composite, or rubber. Alternatively, multiple components of different materials may be connected or fused together. In one embodiment, the plastic is see-through, translucent, or transparent to provide the medical professional additional visibility of all portions of the nose of the patient. As a result, a light source may be connected to the nasal guide 200 so that it may act as a light guide.

In one embodiment, before use or application of the nasal guide 200, the shape of the nasal guide 200 may be molded or fit to a mold or nose of the patient. For example, the nasal guide 200 may be heated in hot water and then formed to the size and shape of the nose of the patient. In another embodiment, one or more pictures, a three-dimensional image, x-ray, MRI, or other scan of the nose may be utilized to create or mold the nasal guide 200. For example, an image may be utilized by an injection molding system to create the nasal guide 200.

The nasal guide 200 may also have anti-fungal, anticoagulant, procoagulant, and/or anti-bacterial properties for preventing the spread of infections from the mouth or lips to the inside of the nose and brain. In one embodiment, the material of the nasal guide 200 may be formulated, molded, impregnated, injected, coated, or otherwise created with any of the described compounds, materials, or properties to prevent any unwanted spread of germs or infection. For example, the nasal guide 200 or an interior portion of the nasal guide 200 inserted into the nose may be coated with an anesthetic agent, such as lidocaine creme to make the nasal guide 200 more comfortable.

In one embodiment, the nasal guide 200 includes a left support 202, a right support 204, a bridge 206, upper lumens 208, lower lumens 210, drains 212, and an elastic 214. In one embodiment, the left support 202 and right support 204 (collectively the "supports") are the supportive framework of the nasal guide 200 that prevents the nasal guide 200 from slipping into the nostrils, and in which the lumens 208, 210 are formed. The supports 202 and 204 may help prevent the nasal guide 200 from slipping during a medical procedure. The supports 202 and 204 may also guard covered portions of the nose from contact with objects, such as medical instrumentation. The left support 202 and right support 204 are each configured to abut, be placed against, adjacent, or proximate left and right portions of the nose and nostrils, respectively. The supports 202 and 204 may also be placed in contact with the columella, philtrum, and upper lip. In one embodiment, the supports 202 and 204 are directly coupled to one another for additional support without the need for a bridge 206.

Figure 3:
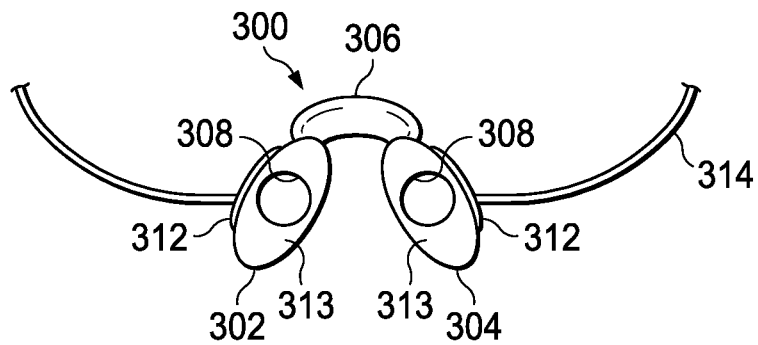
FIG. 3 is a schematic, plan view of a nasal guide in accordance with an illustrative embodiment.

In one embodiment, the supports 202 and 204 may include lateral edges or extensions (not shown) that extend perpendicular to the general plane 213 of the supports 202 and 204 on the outer edges of the supports 202 and 204 for cradling the sides of the nose of the patient during use of the nasal guide 200 (see the lateral edges 312 of FIG. 3 for an example). The supports 202 and 204 may also extend or include extensions to be supported by the cheeks of the patient. For example, in an embodiment of the nasal guide 200 that may be appropriate for intensive surgeries, the supports 202 and 204 may be shaped to extend out to and be braced or flattened against the cheeks of the patient. In one embodiment, the lateral edges (see FIG. 3) stabilize the nasal guide 200 as medical instruments are inserted into and removed through the upper lumens 208 and lower lumens 210. For example, the lateral edges may provide lateral stability. The lateral edges are further shown and described in FIGS. 3 and 7-10.

With reference to FIG. 3, the lateral edges 312 may act as clips for gently securing the nasal guide 300 against the sides of the nostrils during utilization of the nasal guide 300. The lateral edges 312 may be wide enough to secure an entire or substantial portion of the side of the nostril when the nasal guide 300 is attached.

Referring again to FIG. 2, in one embodiment, the nasal guide 200 may include the bridge 206, which may be a connector or other element between the supports 202 and 204. The bridge 206 may be configured so that the angle and position of the left support 202 and right support 204 may be adjusted to fit the size and shape of the nose and nostrils of the patient. The bridge 206 itself and the connection points between the bridge 206 and supports 202 and 204 may be flexible, allowing the nasal guide 200 to be positioned, flexed, or stretched as needed for the patient's nose or medical procedure. This allows the nasal guide 200 to be contoured, or otherwise fitted, to different sized and shaped noses and nostrils. As shown in the various embodiments, the bridge 206 may be placed at, or connected to, the top, middle, or bottom of the supports 202 and 204 or lateral edges or at any position therebetween.

In another embodiment, the nasal guide 200 may include multiple bridges for connecting the supports 202 and 204. For example, bridges may be attached to the top and bottom of the left support 202 and right support 204 curving in the same or different directions (e.g., curving up and down respectively) to allow the bridges to be flexed or stretched as needed to fit the nose of a patient. The bridge 206 or bridges may be connected to the inside or outside edges, top, bottom, or middle of the supports 202 and 204.

In one embodiment, the bridge 206 is positioned between the supports 202 and 204 and attaches to the middle of the supports 202 and 204 on the inside edges to provide maximum flexibility for moving the supports 202 and 204 toward each other and adjusting the angle of the supports to conform to the nostrils. In another embodiment, the nasal guide 200 may not include a bridge 206 and instead the supports 202 and 204 may be directly or flexibly connected to one another. The bridge 206 may be a cylindrically-shaped, rounded, or flattened connector for providing comfort or support when freely positioned away from the nose or positioned against the columella, tip, bridge, or other portion of the nose.

The upper lumens 208 and lower lumens 210 (collectively the "lumens") are tubes or other passageways including openings through which the medical instruments may be inserted or communicated. Alternatively, the lumens 208 and 210 may be referred to as openings, through holes, or guides. The lumens 208 and 210 may be formed by or in the supports 202 and 204, and may be defined by walls that extend through the plane of the supports 202 and 204 such that passageways into the nostrils are provided. In one embodiment, the lumens 208 and 210 may extend substantially perpendicular from the general plane 213 of the supports 202 and 204.

In another embodiment, the walls of the lumens 208 and 210 may be short and extend inward and downward to or into the nasal passage for applying suction within the nose. For example, an interior end of the lumens 208 and 210 may have a tapered end, or open in a scoop or funnel shape for applying suction. In yet another embodiment, the walls of the lumens 208 and 210 may extend or curve slightly upward or to a side from the supports 202 and 204 to better guide medical instruments toward a specific sinus in the nasal cavity. In one embodiment, the nasal guide 200, and particularly the lumens 208 and 210, may be configured to be inserted anywhere from 0-10 centimeters (e.g., 2-10 cm) or more into the nose of the patient. In another embodiment, the nasal guide 200, and particularly the lumens 208 and 210, may not enter the nostrils at all, and instead may be positioned near the opening of the nostrils or extend externally from the nasal guide 200.

The lumens 208 and 210 including the walls thereof, may protrude past the general plane 213 of the supports 202 and 204 to both guide and stabilize medical instruments. In some cases, longer lumens 208 and 210 may simplify performing medical procedures without additional endoscopes, catheters, or instruments. For example, a greater length of the lumens 208 and 210 may better stabilize a portion of the medical instruments inserted through and positioned in the lumens 208 and 210. In one embodiment, either end of the lumens 208 and 210 may be configured to receive inwardly extending or externally protruding extensions. The extensions may be straight or curved or have any of the other properties described for the nasal guide 200 and lumens 208 and 210.

The diameter of the lumens 208 and 210 may vary based on the application. In one embodiment, the opening of the lumens 208 and 210 are between 5 mm-2.5 cm in diameter for human applications, but this may vary. In one embodiment, the size or diameter of the lumens 208 and 210 may be uniform along the length of the nasal guide. In another embodiment, the size of the lumens 208 and 210 may narrow slightly at the interior end allowing the nasal guide 200 to have a more conical or funnel shape for easy insertion of medical instruments. Additionally, the conical or funnel shape may naturally expand the nostrils when inserted.

Also, in one embodiment, any of the openings of the lumens 208 and 210 may be flared, rounded, or tapered so that medical instruments do not catch on internal or external (to the nose) edges of the lumens 208 and 210.

The lumens 208 and 210 may utilize any number of symmetrical or asymmetrical shapes, such as circles, ellipses, polygons, tear drop shapes, etc. The walls may similarly define these shapes extending from the supports 202 and 204. In another embodiment, the lumens 208 and 210 and corresponding walls may form a cylindrical, conical, or hyperbolic shape extending into the patient's nasal cavities when the nasal guide 200 is inserted as shown in FIGS. 6-10. In one embodiment, both ends of the lumens 208 and 210 may be flared and rounded to prevent medical instruments from catching on the openings as medical instruments are inserted and removed from the nose of the patient. In one embodiment, the openings of the lumens 208 and 210 may be at least partially covered with a flexible material and have one or more slits, slots, notches, or perforations (e.g. forming a diaphragm or membrane with an opening) for sliding the medical instruments in and out. For example, the openings of the lumens 208 and 210 may be like the lid of a cup adapted to receive a straw. The slits may support the medical instruments and prevent the spread of fluids or leakage of fluids.

In one embodiment, the lower lumens 210 may be positioned lower on the supports 202 and 204 for use in applying suction through the nasal guide 200. For example, during a medical procedure, mucus, blood, or other fluids may pool against the supports 202 and 204 of the nasal guide 200. The lower lumens 210 may be positioned to suction out these fluids. In one embodiment, the lower lumens 210 may be short to allow the fluids to flow out of the nasal guide 200 through the lower lumens 210. In another embodiment, inwardly-extending walls of the lower lumens 210 may extend straight or at an angle to be proximate or touch a bottom portion of the nasal cavity where fluids are most likely to collect. The inwardly-extending walls may also extend at an angle to a general plane 213 of the supports 202 and 204.

In another embodiment, one or both of the lumens 208 and 210 may also extend outwardly from the nostrils and define ports for applying or attaching traditional oxygen or suction fittings, adapters, systems, or devices, such as an oxygen system (e.g., through a nasal cannula), or tubes. Alternatively, the interior or exterior portions of the lumens 208 and 210 may be configured to receive adapters (not shown) for attaching suction or oxygen through the nasal guide 200 or extending the reach or direction of the lumens 208 and 210. The shape and configuration of the adapters may also vary. For example, the adapters may be funnel shaped for receiving medical instruments. Alternatively, the adapter may include a 90° bend for reaching a particular sinus.

In one embodiment, the adapters may be inserted into the lumens 208 and 210 and may remain in place due to tight tolerances and friction between the lumens 208 and 210 and adapters, or provide an interference fit. In another embodiment, the lumens 208 and 210 and adapter may include threads, barbed connectors, or locking tabs allowing the adapter to be screwed into the nasal guide 200. For example, immediately after a medical procedure is performed, oxygen and/or suction may be attached to the nasal guide without using other instruments. As a result, time and resources may be saved without further inconveniencing the patient by adding and removing additional components. The lumens 208 and 210 may then act as nozzles for delivering oxygen or for coupling suction ends to apply suction to the nasal cavity of the patient. Oxygen or suction may also be applied to the lumens 208 or 210 during a medical procedure as needed. For example, the oxygen may be applied during the procedure to keep the interior of the nose dryer. In one embodiment, the interior end of the lumens 210 may be formed in the shape of a scoop that fits within the nasal passage to channel any blood, mucous, or fluids through the lumens 210 for removal. The scoop end of the openings on the internal side of the nasal guide may be wide enough to fit along the entire width of the bottom and sides of the nasal passage to channel the fluids through the lumens 210.

In one embodiment, the lumens 208 and 210 may not extend past the general plane 213 of the supports 202 and 204. Instead, the lumens 208 and 210 may extend away from the nose and nostrils of the patient when positioned on the patient. As a result, the lumens 208 and 210 may not irritate the patient's nasal cavity. Exterior lumens may similarly stabilize and guide medical instruments to the correct position. Alternatively, a combination of internally and externally lumens 208 and 210 may be utilized. For example, the nasal guide 200 may include additional guides, rings, or other supports for supporting a portable endoscope as is subsequently described. In one embodiment, the lumens 208 and 210 may be dilated, collapse, or include a circularly folding structure for adjusting the diameter of each lumen. As a result, the size of the lumens 208 and 210, or other components of the nasal guide 200 may be customized for the patient.

In another embodiment, the nasal guide 200, the supports 202 and 204, and the lumens 206 and 208 may be cut down or sized to fit the patient. In one embodiment, the nasal guide 200 may include perforations (or thinner or weaker areas) for cutting or breaking away sections of any portion of the nasal guide for customization for the patient. The nasal guide 200 may also include markings, such as metric or English unit measurements, for properly sizing and utilizing the nasal guide 200. Such markings may be inscribed, molded, etched, printed, or otherwise included on the nasal guide 200.

In one embodiment, the nasal guide 200 may include drains 212. The drains 212 may be one or more openings, slits, or notches through a portion of the nasal guide that allows fluid to pass through, below, or around the nasal guide 200. The drains 212 may allow fluids to bypass the nasal guide 200 to be dealt with in any number of ways. The drains 212 may utilize any number of shapes or configurations. In one embodiment, the drains 212 may be semicircular, rectangular, or square shaped. In another embodiment, the drains 212 may be a single cut-away portion of the supports 202 and 204 allowing the fluids to flow under the supports 202 and 204 For example, the fluids may be soaked up by gauze or suctioned by the medical professional once past the supports 202 and 204 of the nasal guide 200.

In one embodiment, the supports 202 and 204 may include a clip, or other attachment mechanism, for attaching gauze in such a way that the gauze absorbs the fluid that passes through the drains 212 without interfering with insertion or removal of medical instruments through the lumens 208 and 210. The clip may also be utilized to attach to the end of a suction device. The clip may extend from any surface or edge of the supports 202 and 204.

The nasal guide 200 may include headgear or other securing component, device, or mechanism. In one embodiment, the headgear is the elastic 214. The elastic 214 is a fastener usable to secure or stabilize the nasal guide 200 during use. In one embodiment, the elastic 214 is an elastomer or other stretchable material that may be utilized to secure the nasal guide 200 about the head, ears, personal or medical accessories (i.e., glasses), or neck of the patient. The elastic 214 may attach to the supports 202 and 204 or the lateral edges of the supports 202 and 204. The elastic 214 may be one or more narrow or wide bands. The wider band may provide additional surface area and more comfort to the user. For example, the elastic 214 may be neoprene straps that are secured around the neck or head of the patient utilizing a hook and loop strap, barbed connector, Velcro, buckle, or other known securing mechanism on either end of the neoprene straps. In one embodiment, the headgear may be attached to and removed from the nasal guide for repeated use. The headgear may be configured to be washed or otherwise sanitized as needed.

In one embodiment, the elastic 214 is formed of or covered by a cloth material for the comfort of the patient. The elastic 214 may have a high elastane content for adjusting to the size and shape of the applicable portion of the patient (e.g., head, neck, or ears), including adults or children. As with other elastics, a portion of the elastic 214 may be pulled through holes of the supports 202 and 204 (or lateral edges of the supports 202 and 204) to tighten the fit of the nasal guide when worn by the patient. Alternatively, a belt strap-type configuration may be utilized for the elastic 214. Any number of adjustment mechanisms or components may be utilized with the elastic 214 or other securing mechanism to properly fit the nasal guide 200 to the patient. Skin glue, tape, or other similar components may be utilized in a stand-alone configuration or with the elastic 214 to secure the nasal guide 200.

In one embodiment, the nasal guide 200 may include a single support, such as the support 202, and no bridge 206. The elastic 214 may be attached to either or both sides of the support 202 and may be used for situations where the medical professional(s) only needs access through the nostril on one side, or any single opening on the patient's body. Alternatively, the nasal guide 200 may be moved between nostrils to save materials and expense of manufacturing. In one embodiment, the nasal guide 200 may be used a single time before being disposed. The nasal guide 200 may also be configured for repeated use, including repeated use after sterilization. For example, the nasal guide 200 may be run through and sanitized by an autoclave without being ruined or altered. The single support size of the guide may also be utilized for other natural or surgically-created orifices or body parts. For example, the support 202 may conform to the shape of an ear, buttocks, incision in the abdomen, and so forth.

In one embodiment, the nasal guide 200 may include differently-sized or shaped supports 202 and 204 that may be linked by the bridge 206 such that the support 202 has a different size or shape than the support 204. For example, a patient with an irregular nose or nasal valve collapse may require that the supports 202 and 204 and/or lumens 208 and 210 be differently sized or shaped for each size or shape of the nose. In one embodiment, the bridge 206 or supports 202 and 204 may be separately created (e.g., molded), clipped, or otherwise attached to one another to be customized for the patient.

In another embodiment, the supports 202 and 204, lumens 208 and 210 (whether single openings or multiple openings are utilized), and corresponding framework or walls may be referred to as nozzles.

In another embodiment, the nasal guide 200 may include interchangeable components that allow a medical professional to customize or assemble the nasal guide 200 for each patient. For example, the supports 202 and 204 and bridge 206 may be the framework or support structure of the nasal guide 200 that may be selected. The supports 202 and 204 may be configured to receive a lumen module (not shown). The lumen module may be a fitting adapted to be connected to each of the supports and includes one or more lumens. In one embodiment, the lumen module may be conically shaped for expanding each nostril as is described herein. In one example, the lumen module may include three 2 mm lumens for receiving multiple instruments. The number of lumens 208 and 210 utilized in the nasal guide 200 is not limited, but may be between 1-6. In another example, the lumen module may include one 8 mm lumen or two 4 mm lumens. The lumen module may be attached or removed from each of the supports 202 and 204. As a result, the nasal guide 200 may be utilized repeatedly by assembling the distinct parts for each patient. In one embodiment, the medical professional may include various sizes and configurations for each of the components of the nasal guide 200 for adapting the nasal guide 200 for each individual patient and medical procedure.

FIG. 3 is a schematic, pictorial representation of a nasal guide 300 in accordance with another illustrative embodiment. The nasal guide 300 of FIG. 3 may include a left support 302, a right support 304, bridge 306, lumens 308, lateral edges 312, and an elastic 314.

In this embodiment, the supports 302 and 304 are oval shaped to more closely fit the size and shape of certain nostrils and noses. For example, the supports 302 and 304 may be positioned to abut against the bottom portion of the noses with the lumens 308 extending into the nostrils and toward the nasal cavities. As shown in FIG. 3, each of the supports 302 and 304 forms a respective lumen 308 for receiving one or more medical instruments. In one embodiment, the lumens 308 are larger for receiving a larger single instrument or multiple instruments at once.

In the nasal guide 300, the bridge 306 may be shaped differently for various functions. In this embodiment, the bridge 306 is configured to support, surround, or cup the tip of the nose of the patient. For example, the bridge 306 may be shaped to extend along the bottom of the nose of the patient with a portion of the bridge 306 being substantially rounded or bent to conform to the typical rounded shape of the tip of a patient's nose.

The nasal guide 300 may also include lateral edges 312. The lateral edges 312 are stabilizers configured to support or abut the lateral, or side, edges of the nose to provide external alignment with the nostrils. The lateral edges 312 may extend substantially perpendicularly from the surface or general plane 313 of the supports 302 and 304, and may also extend toward the face of the patient when the nasal guide 300 is in use. The lateral edges 312 may further stabilize the nasal guide 300 during use and performance of a medical procedure. In one embodiment, the lateral edges 312 may be elongated semicircles. In another embodiment, the lateral edges 312 may be small arms, tabs, clips, or extensions that are shaped as a square, rectangular, or elliptical. The lateral edges 312 and other portions of the nasal guide 300 may be padded or include an additional material to make the nasal guide 300 more comfortable when positioned against the skin.

In one embodiment, the lateral edges 312 may help secure the nasal guide by holding, or abutting against the outside of the nose while the lumens 308 abut against the inside of the nose. For example, the lateral edges 312 and outer walls of the lumens 308 may act as a clip securing the nasal guide 300 to the inside and outside of the edges of the nostrils.

Figure 4:
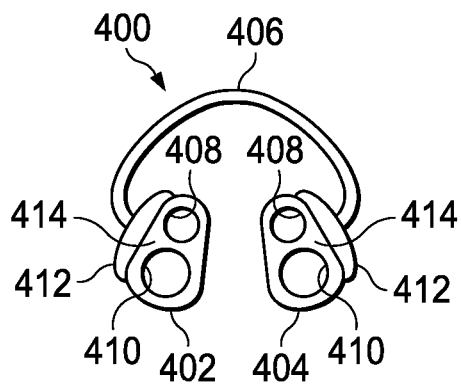
FIG. 4 is a schematic, plan view of another nasal guide in accordance with an illustrative embodiment.

FIG. 4 is a schematic, plan view representation of a nasal guide 400 in accordance with another illustrative embodiment. The nasal guide 400 includes upper lumens 408 and lower lumens 410 that are differently sized for receiving medical instruments. The size and shape of the upper lumens 408 and lower lumens 410 may depend on the type of medical procedure being performed and the medical instruments involved. The upper lumens 408 and the lower lumens 410 may be positioned horizontally (side-by-side), diagonally, or in any other position with respect to one another.

The nasal guide 400 includes a bridge 406 that is also configured as a clip. The bridge 406 may be biased to push the supports 402 and 404 toward each other and secure the nasal guide 400 on, within, and to the nose of the patient. In another embodiment, the bridge 406 may be biased to push the supports 402 and 404 away from each other to further expand the nostrils of the patient while still securing the nasal guide 400. The bridge 406 may secure the nasal guide 400 without the need for elastic or other securing mechanisms. The bridge 406 may be integrated with or attach to the lateral edges 412 or directly to the supports 402 and 404. In one embodiment, the bridge 406 is substantially within the general plane 414 of the supports 402 and 404. The bridge 406 may also be angled such that the top of the bridge 406 extends in front of or behind the supports 402 and 404 (e.g., outward or inward with respect to the user's face when the nasal guide 400 is positioned on the user). In another embodiment, the bridge 406 may connect to the lateral edges 412 and extend away from the general plane 414 of the supports 402 and 404 above the bridge of the nose.

In one embodiment, the bridge 406 may be sized and shaped such that the bridge 406 does not touch the nose of the patient. In another embodiment, the bridge 406 may abut the outside edge of the nose of the patient to provide another point of contact for stabilizing the nasal guide. In one embodiment, the bridge 406 may include a shield, or blinders, clips, or attachments for such components, to prevent the patient from seeing the insertion and removal of the medical instruments. For nervous, fearful, or scared patients that are awake, blocking the sight of the patient may help the patient to not focus on what may be seen. In addition, the tactile sensation of the nasal guide 400 may help the patient not focus on the medical procedure being performed. The interior and exterior of the nose includes a large number of nerves. The sensation of the nasal guide being inserted and worn may distract the user from more significant pain or sensations that results from performance of the medical procedure.

Figure 5:
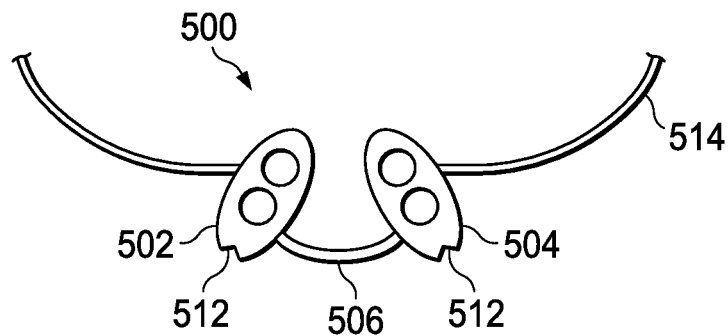
FIG. 5 is a schematic, plan view of another nasal guide in accordance with an illustrative embodiment.

FIG. 5 is a schematic, pictorial representation of a nasal guide 500 in accordance with another illustrative embodiment. The nasal guide 500 further illustrates a bridge 506 positioned at a middle or bottom portion of the supports 502 and 504. The positioning and interconnection of the bridge 506 and elastic 514 may be configured to best fit different sizes and shapes of noses. Drains 512 may be shaped as a single opening for allowing the fluid to flow past the supports 502 and 504. For example, the drains 512 may be rounded in the form of a semi-circle for the comfort of the user.

Figure 6:
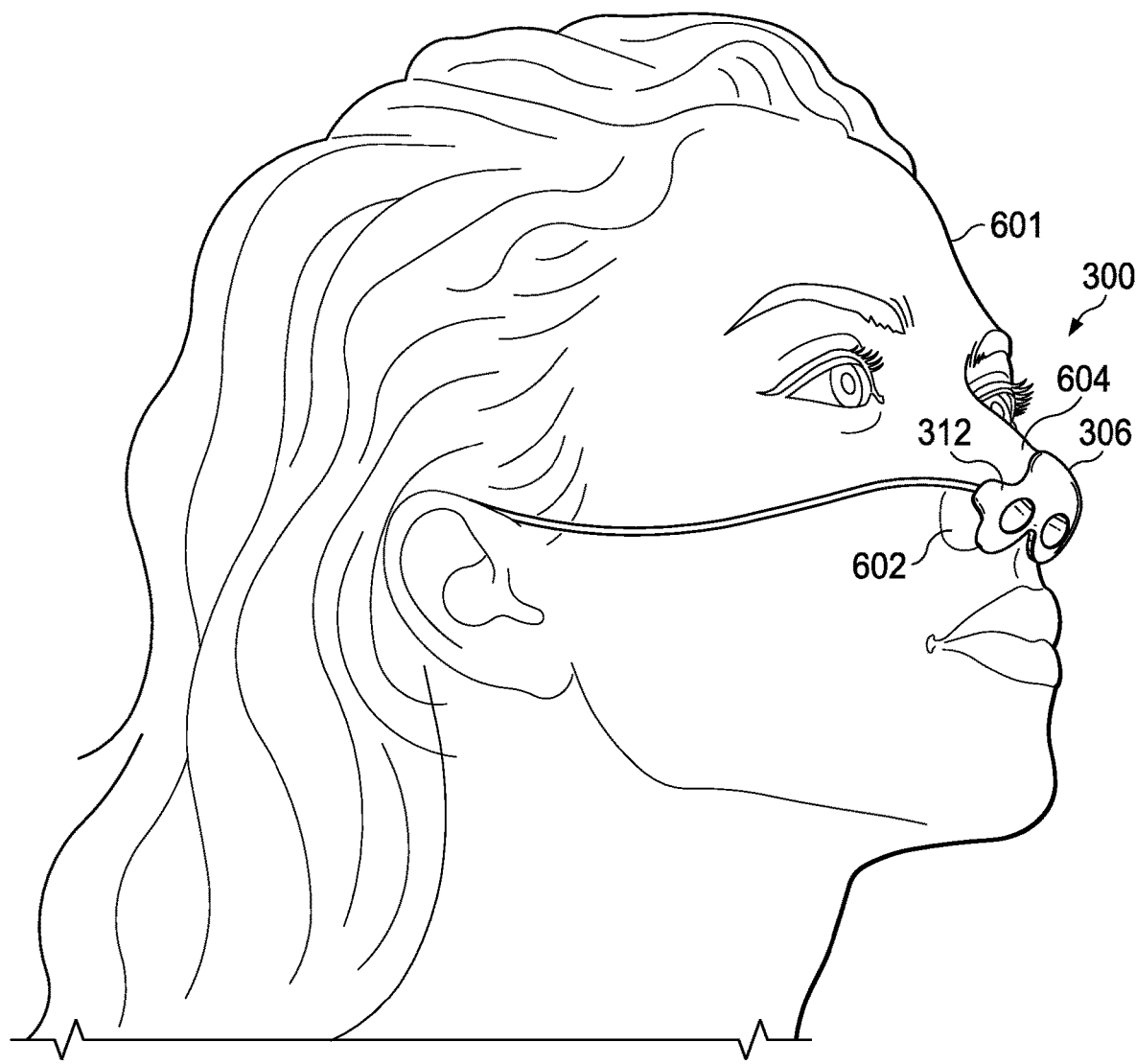
FIG. 6 is a schematic, pictorial representation of another nasal guide installed on a patient in accordance with an illustrative embodiment.

FIG. 6 is a perspective pictorial representation of the nasal guide 300 of FIG. 3 applied to a patient 601 in accordance with an illustrative embodiment. The nasal guide 300 of FIG. 6 illustrates utilization of the nasal guide 300 on a nose 602 of a patient 601. The lateral edges 312 wrap around the edge of the nose 602 to further secure the nasal guide 300 from horizontal motion during the medical procedure.

The bridge 306 may cup or support the tip of the nose 602 to provide vertical support. The bridge 306 may also wrap around the entire tip of the nose 602 to further secure the nasal guide 300 from vertical motion during the medical procedure. In other embodiments, the bridge 306 may be flattened or rounded to abut against the bottom of the nose 602 when the nasal guide 300 is positioned. In yet another embodiment, the bridge 306 may extend back or up from the supports 302 and 304 toward the eyes of the patient 601. In such a configuration, the nasal guide 300 may sit along a top 604 or bridge of the nose 602.

Figure 7:
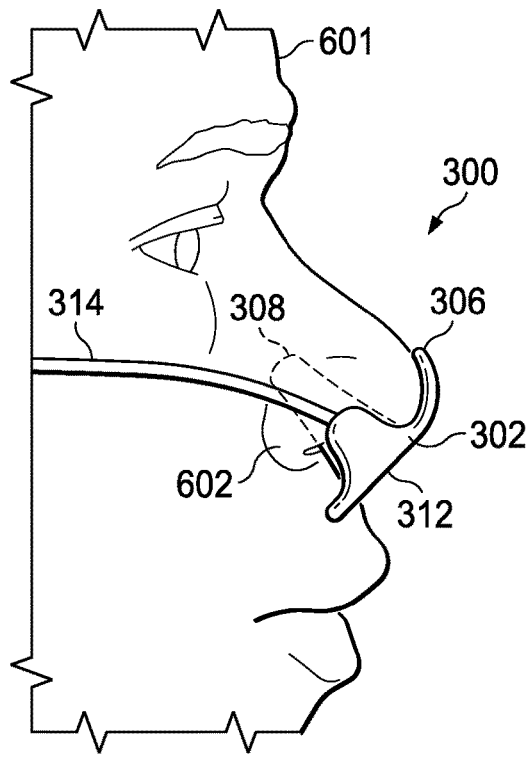
FIG. 7 is a schematic, side-view of a nasal guide in accordance with an illustrative embodiment.

FIG. 7 is a schematic, side view of the nasal guide 300 of FIG. 3 in accordance with an illustrative embodiment. FIG. 7 further illustrates a potential shape and configuration of the nasal guide 300 for adding additional horizontal and vertical stability. The support 302, bridge 306, and lateral edge 312 stabilize the nasal guide 300 vertically and horizontally. In addition, the lumens 308 are shaped to extend inward from the supports 302 and 304. Although not shown, the nasal guide 300 may include both supports 302 and 304 from which the lumens 308 extend.

In one embodiment, the lumen 308 is conically-shaped and extends into the nasal cavity of the patient 601 during use. The cone or wedge shape of the lumens 308 that extends from the openings in the supports 302 and 304 may be useful for naturally expanding the nostrils of the patient 601 as the nasal guide 300 is inserted and the pulled towards the face of the patient 601 by the elastic 314. The cone shape of the lumens 308 facilitates natural expansion of the nostrils without causing the patient 601 pain. As a result, the medical instruments may be more easily inserted and removed from the nose 602. The lumens 308 may include a solid surface ensuring that medical instruments do not catch or snag during insertion or extraction through the nasal guide 300. In another embodiment, the lumens 308 may have a spaced surface for saving material. For example, a honeycomb or triangular support framework may support the one or more lumens 308 that are part of the nasal guide 300.

In one embodiment, the lumens 308 may curve slightly upward to better guide medical instruments to the sinuses and nasal cavity. For example, the supports 302 and 304 may sit flat against the bottom of the nostrils and the curved shape of the lumens 308 may better guide medical instruments. In one embodiment, the interior surface of the lumens 308 may also include ridges (not shown) that run parallel to the nasal cavity for better guiding the medical instruments. The ridges may be flexible for providing additional support to the medical instruments while still allowing the medical instruments to be maneuvered and moved as needed. In another embodiment, the interior portion of the lumens 308 may include flexible extensions, protuberances, or arms (not shown) that further stabilize the medical instruments while providing a small amount of friction or tactile feedback to the medical professional. The flexible protuberances may be configured to give way and bend when the medical professional moves the medical instruments, but also provide support while the medical instruments are in use. The flexibility, diameter, length, proximity, and number of protuberances may vary based on the amount of resistance that is desired. As a result, motion of the medical instruments is slightly opposed to provide enhanced stability and smoothness to the movements of the medical instruments.

The lumens 308 may utilize a solid conical shape. The solid lumens 308 prevent the medical instruments from catching on the lumens 308 when inserted and removed from the nasal guide 300. The ends of the lumens 308 at the interior and exterior openings may flare or taper outward so that the medical instruments do not catch on the edges of the lumens 308 during use. Alternatively, the lumens 308 and other portions of the nasal guide 316 may include cut-outs or integrated spaces for conserving the material utilized to form the nasal guide 300 when molded or assembled. The spaces may also provide additional flexibility to all or portions of the nasal guide 300. As a result, the nasal guide 300 may be deformed while being positioned on the patient 601 to best fit the nose 602 of the patient 601.

In one embodiment, the nasal guide 300 may be injection molded from a single piece of material in default or custom sizes and configurations. For example, the openings and overall size of the nasal guide 300 may be created to specifically fit the nose 602 of the patient 601 based on a picture or scan. The picture or scan may be digitized and utilized to properly size the nasal guide 300. In another embodiment, the different portions of the nasal guide 300 may be formed from different materials. For example, the lateral edges 312 may be formed of a more flexible material (e.g., plastic, latex, etc) for adjusting to the size and shape of the nose 602 of the patient 601. The bridge 306 may be formed of a stiffer form of plastic for providing additional support.

Figure 8:
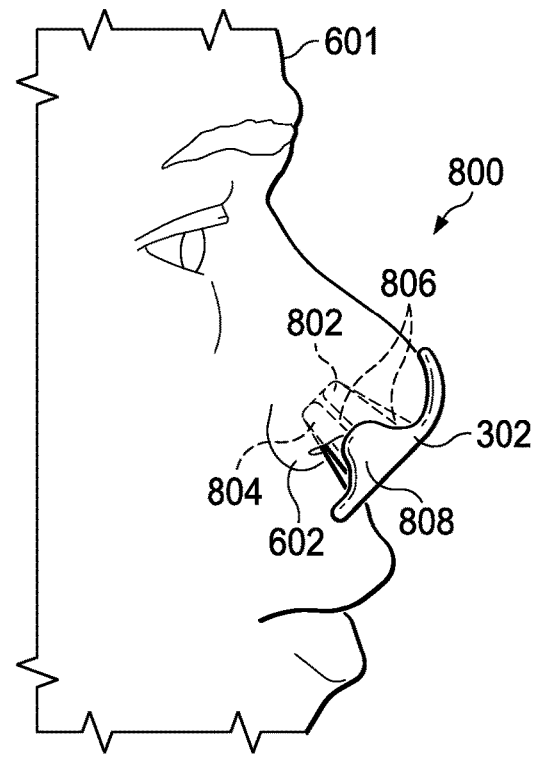
FIG. 8 is a schematic, side-view of another nasal guide in accordance with an illustrative embodiment.

FIG. 8 is a schematic, side-view of a nasal guide 800 in accordance with another illustrative embodiment. The nasal guide 800 includes multiple openings at ends of the lumens 802 and 804 instead of a single opening. The nasal guide 800 may include additional supports 806 between the lumens 802 and 804 and the supports 302 (and 304 not shown) of the nasal guide 800. The framework of the nasal guide 300 including the additional supports 806 may prevent deformation of the nasal guide 800 and the lumens 802 and 804 during insertion and removal of medical instruments. For example, the additional supports 806 may provide a framework enclosing the lumens 802 and 804 within a conical shape. In another embodiment, the supports 806 may enclose the lumens 802 and 804 with a cylindrical shape. The nasal guide 800 may clip to the nostrils of the nose 602 of the patient 601 with the lateral edges of the nostrils being secured between the lateral edges 808 and the supports 806 (or alternatively between the lateral edges 808 and the lumens 802 and 804).

Figure 9:
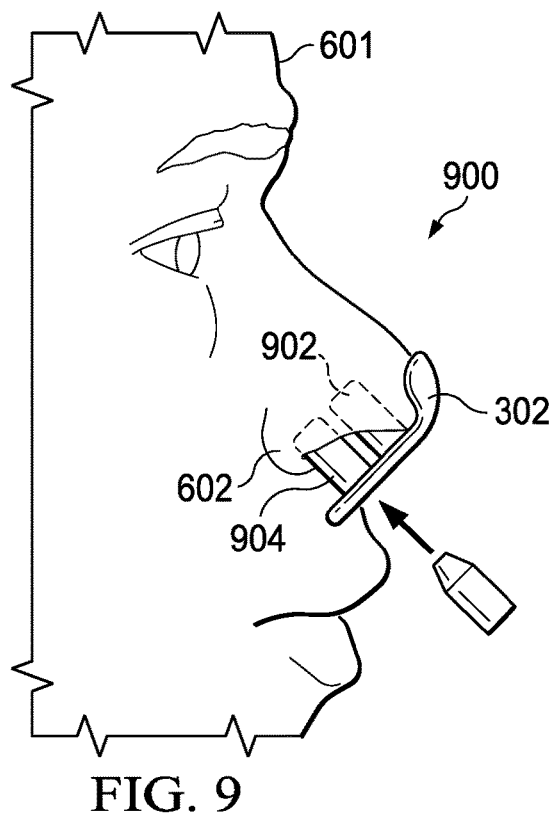
FIG. 9 is a schematic, side-view of another nasal guide in accordance with an illustrative embodiment.

FIG. 9 is a schematic, side-view of a nasal guide 900 in accordance with an illustrative embodiment. The nasal guide 900 may include multiple openings with walls or supports defining the lumens 902 and 904 that extend inward to a nasal cavity of a patient. In one embodiment, the lumens 902 and 904 may be defined separately and extend from the supports 302 (and 304 not shown) of the nasal guide 900. The lumens 902 and 904 may have a gap, or notch, between them.

Figure 10:
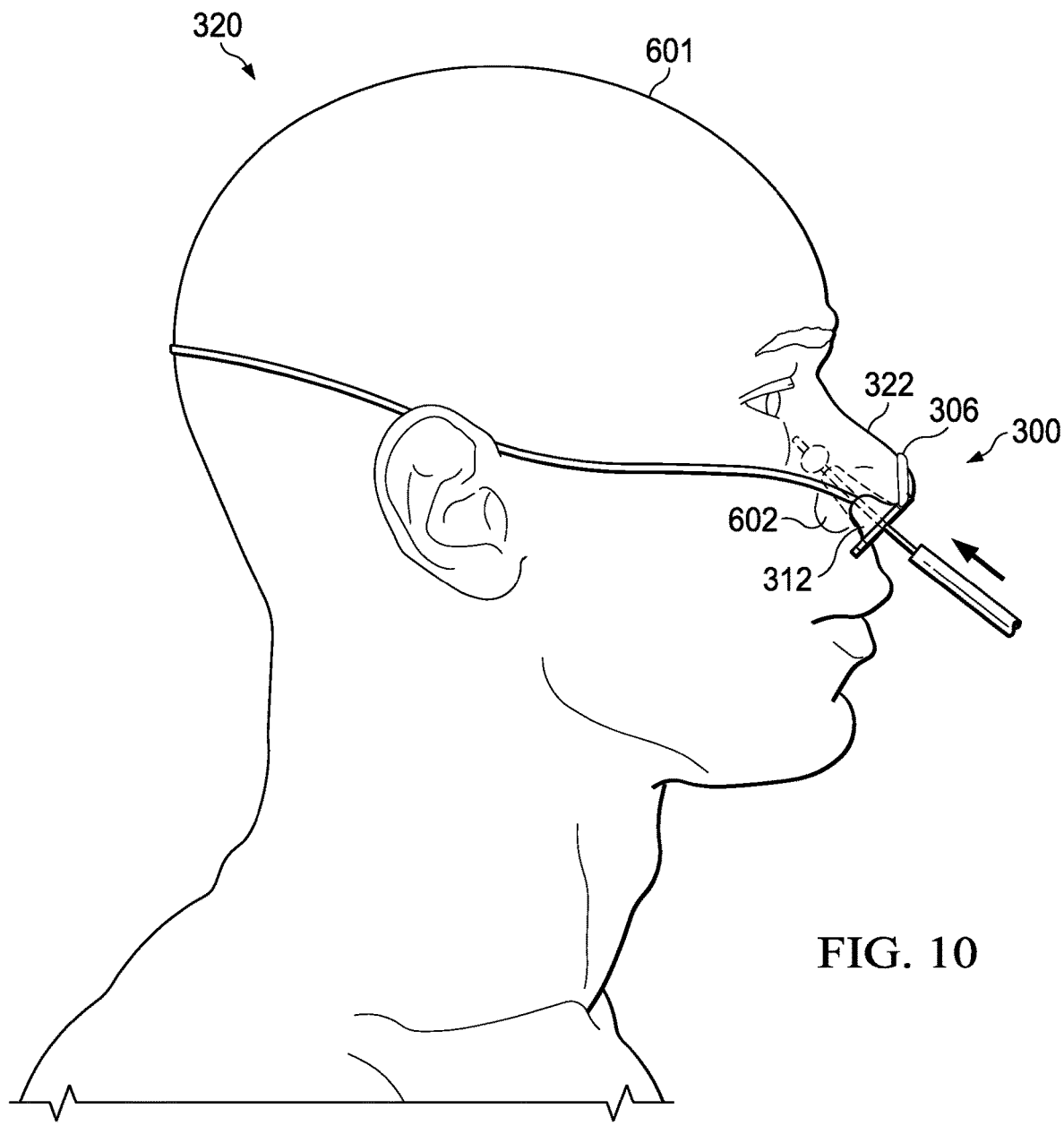
FIG. 10 is a schematic, side view of a nasal guide being utilized on a patient in accordance with an illustrative embodiment.

FIG. 10 is a schematic, side-view of the nasal guide 300 being utilized on a patient 601 in accordance with an illustrative embodiment. In one embodiment, the nasal guide 300 may be utilized to protect the nose 602 of the patient 601 during a medical procedure, such as balloon sinuplasty. The bridge 306 may touch the nose 602 of the patient 601 during use. The lateral edges 312 may abut the lateral edges of the nostrils to provide lateral support.

Figure 11:
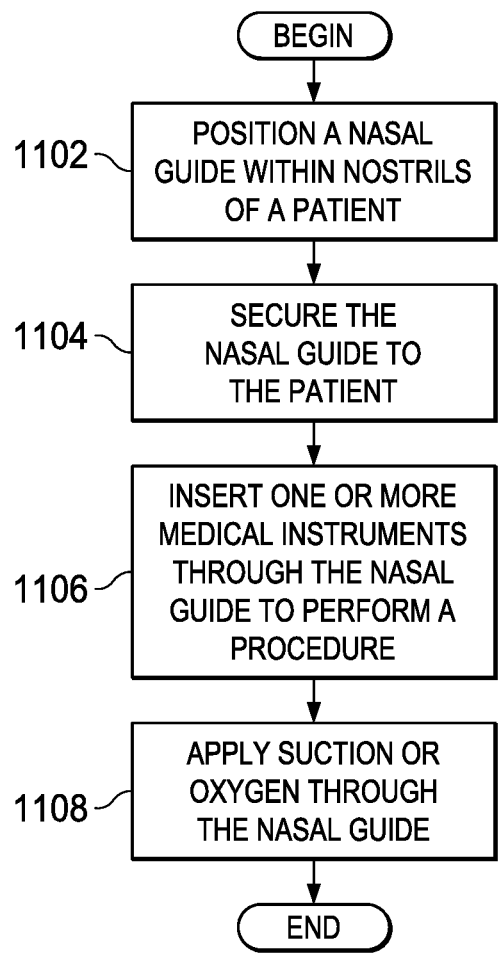
FIG. 11 is a flowchart of a process for utilizing a nasal guide in accordance with an illustrative embodiment.

FIG. 11 is a flowchart of a process for utilizing a nasal guide in accordance with an illustrative embodiment. The process of FIG. 11 may be implemented by a medical professional, or any other person, utilizing a nasal guide on a patient as is illustrated in FIGS. 6 and 10.

The process may begin with the medical professional positioning a nasal guide within nostrils of a patient (step 1102). In one embodiment, only the lumens (and supporting framework) of the nasal guide are inserted into the nostrils extending to the nasal cavity of the patient. The medical professional may select the nasal guide based on the size and shape of the nose of the patient. For example, the selected nasal guide may be substantially smaller for a child. The nasal guide may also be selected based on the size and shape of the medical instruments that are utilized in performing the procedure. For example, a light source and an endoscope with a balloon may need to be inserted into the nostrils simultaneously. As a result, the medical professional may select a nasal guide with two lumens. In another embodiment, the guide is configured to receive a wired or portable endoscope or other medical instrument through naturally or surgically-created openings, including, but not limited to, laparoscopic, abdominal, pelvic, chest, head, neck, intracranial, ear, extremity, cardiac or vascular procedures or diagnostic evaluations.

In another embodiment, the nasal guide may be created, customized, molded, or manufactured to meet the size and shape of a particular patient's nose. In addition, the medical professional may select nasal guide attachments that may be attached to the nasal guide to apply suction and/or oxygen to the patient before, during, or after the medical procedure. The nasal guide may also be configured to act as a wave guide, be illuminated, or glow in the dark. For example, a light source, when shined into the nasal guide, may light up the interior and exterior portions of the nasal guide.

In one embodiment, the portion of the nasal guide that is inserted within the nostril(s) may have a conical shape for enlarging the nostrils as the nasal guide is drawn into the nostril(s) of the patient by a securing mechanisms, such as an elastic fastened around the neck or head of the patient. The elastic or securing band may gently open the nostrils providing easier access to the nasal cavities and sinuses.

Next, the medical professional secures the nasal guide to the patient (step 1104). As previously described, the nasal guide may be secured in any number of ways including elastics, headgear, straps, clips, adhesives, draped configurations, and so forth. The nasal guide may be adjustable (e.g., tightening bands, Velcro, securing holes, etc.) and may be secured to any portion of the body, clothes, or accessories of the patient, such as any portion of the head, neck, or ears.

The nasal guide may also be connected to protective glasses. In one embodiment, the securing portion of the nasal guide is draped around the ears of a patient similar to a nasal cannula.

Next, the medical professional inserts one or more medical instruments through the nasal guide to perform a procedure (1106). The medical instruments may be inserted into and retracted from the nostrils and nasal passage any number of times. The nasal guide guides the medical instruments into the nasal passage during insertion. In one example detailing use of the nasal guide, a single medical professional rather than multiple medical professionals may perform a medical procedure. The nasal guide may be utilized to ensure that the medical instruments are positioned correctly to prevent abrasion, stabbing, or scraping the bone or tissue within the nasal passages or the interior and exterior of the nostrils. In addition, the nasal guide stabilizes the instruments in the nose to allow for ease of manipulation during the procedures especially if the patient moves or sneezes.

In one embodiment, the medical professional may apply suction or oxygen through the nasal guide (step 1108). The nasal guide may be utilized to provide suction or oxygen before, during, or after the procedure. For example, the nasal guide may be configured for simultaneously performing the medical procedure through a first lumens as well as applying suction or oxygen through a second lumen or through a separate side of the nasal guide. An attachment or insert may be built-in, inserted, or attached to the nasal guide to apply suction or oxygen for the patient. In one example, one or more adapters may be inserted or screwed into the openings of the lumens to provide suction or oxygen to the patient. Application of suction or oxygen through the nasal guide provides flexibility for rapidly-developing situations. For example, immediately after a surgery a patient may need to receive oxygen to stimulate recovery. As a result, the nasal guide may serve a dual-purpose. In addition, the nasal guide may be utilized to secure oxygen or apply suction for patients that are seizing, moving, or otherwise unable to receive oxygen or suction through traditional means.

Figure 12:
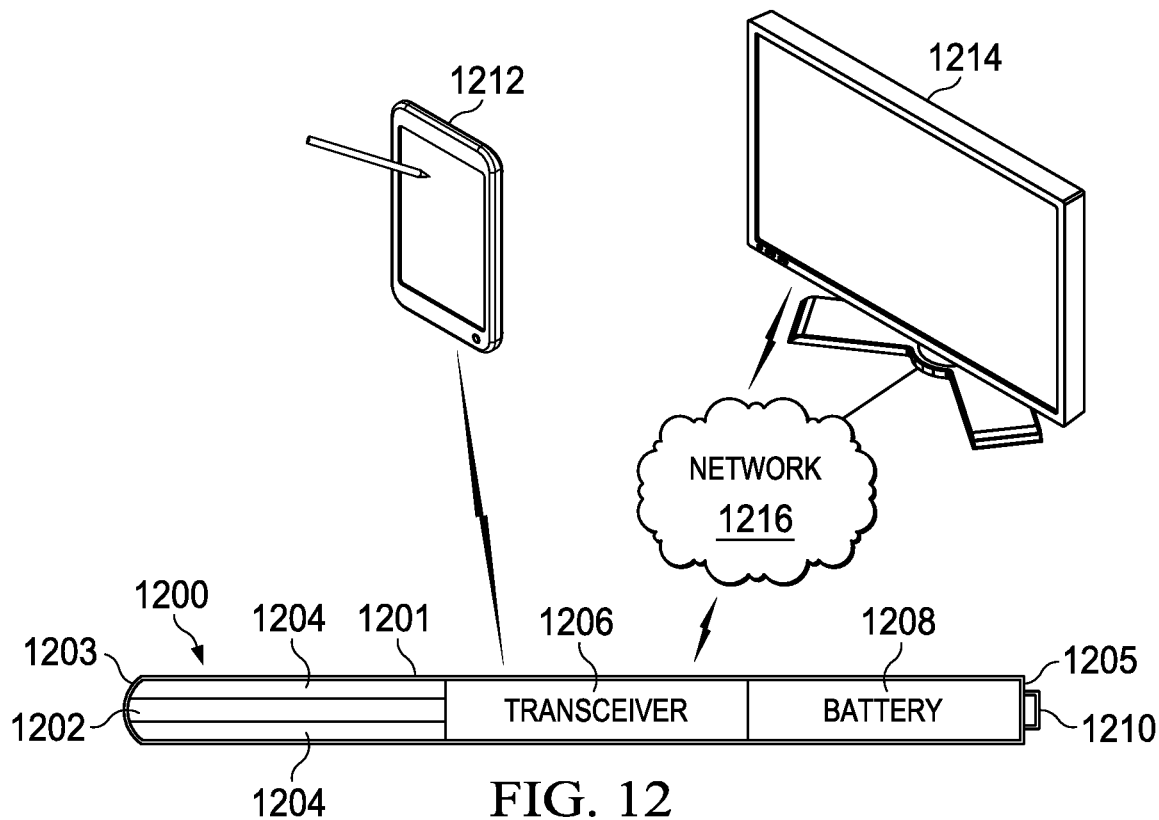
FIG. 12 is a schematic, pictorial representation of a portable endoscope in accordance with an illustrative embodiment.
Figure 13:
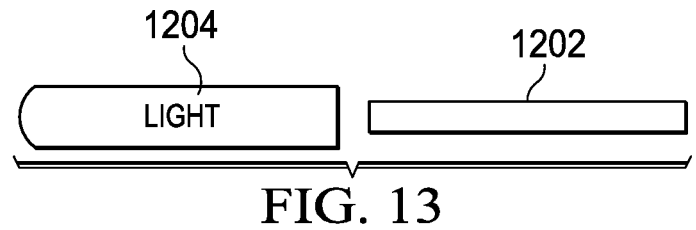
FIG. 13 is a schematic, side view of a cylindrical light and camera in accordance with an illustrative embodiment.
Figure 15:
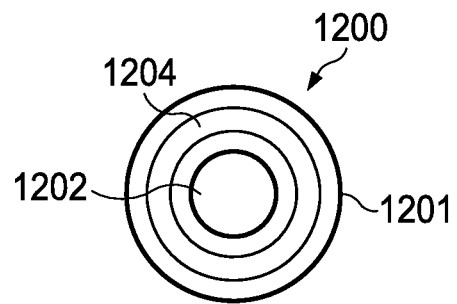

Turning now to FIGS. 12, 13 and 15, a schematic, pictorial representation of a portable endoscope 1200 is shown in accordance with illustrative embodiments. An endoscope is an instrument that may be introduced into the body of an individual or patient to give a view of internal parts. The portable endoscope 1200 may be utilized in very small spaces and is easier to use than existing endoscopes. Existing endoscopes are generally bulky and not ergonomically shaped and may require two or more medical professionals to operate effectively (e.g., a doctor and nurse). In one embodiment, the portable endoscope 1200 is a wireless scope that is condensed into a reduced footprint or size. The portable endoscope 1200 may be utilized by a single user or positioned a single time or as needed within a nasal guide to free up hands of the medical professional.

The portable endoscope 1200 may be cleaned for repeated use or may be a disposable one-time use portable endoscope 1200. The portable endoscope 1200 may be a wand or cylindrical-shape for easy handling by a medical professional. In one embodiment, the portable endoscope has a diameter or cross-sectional measurement of between 1 mm to 5 mm, although the diameter may vary widely depending on the particular application.

The portable endoscope 1200 may be a stand-alone device or may be utilized or integrated with the nasal guide as herein described. For example, the portable endoscope 1200 may be built into one or more of the lumens of the nasal guide. The portable endoscope 1200 may also be attached to or inserted into the nasal guide.

Figure 14:
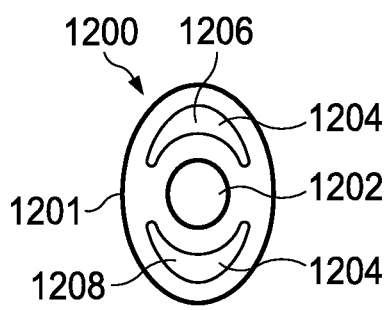
FIGS. 14 and 15 are schematic, front views of the portable endoscope in accordance with illustrative embodiments.

As shown in the schematic front views of FIGS. 14 and 15, the portable endoscope 1200 may be shaped as a circle, oval, ellipse, or a rounded triangle shape. The portable endoscope 1200 may be utilized for any number of medical or non-medical procedures or examinations that are known in the art. In one embodiment, the portable endoscope 1200 is configured to be received by an opening, lumen, or port of the nasal guide as herein described. The portable endoscope 1200 may be inserted to a required depth and positioned to display a video image to the medical professional. In one embodiment, friction, tight tolerances, or interference fittings of the opening and external dimensions of the portable endoscope 1200 may be utilized to secure the portable endoscope 1200 in the nasal guide. In an alternative embodiment, the nasal guide may include a positioning motor for moving the portable endoscope 1200 in and out, rotating the portable endoscope 1200, or otherwise positioning the portable endoscope 1200 within the examined space. The same may be performed for a camera 1202 without moving the remainder of the portable endoscope.

In one embodiment, the portable endoscope 1200 may include the camera 1202, a light 1204, a transceiver 1206, a battery 1208, and a switch 1210. The portable endoscope 1200 may be enclosed in a case 1201. In one embodiment, the case 1201 is a waterproof framework completely sealing in and securing the components of the portable endoscope 1200. The case 1201 may include any number of seals and watertight connections ensuring that the portable endoscope 1200 may be utilized multiple times without damage from fluids. For example, the case 1201 may be formed entirely of a metal, polymer, plastic, or glass. In another embodiment, different components and materials may be fused together. For example, the main body of the case 1201 may be formed of stainless steel with a glass end or lens (not shown) for the light 1204 to shine through and the camera 1202 to retrieve video images.

In one embodiment, the case 1201 includes the contacts, interfaces, wires, or busses for each of the internal electrical components. For example, the camera 1202 and/or light 1204 may contact a video bus integrated within the frame for transmitting the video signal to the transceiver 1206 for transmission. The light 1204 may also include an interface for communicating video signals from the camera 1204 to the case 1201 or directly to the transceiver 1206. In one embodiment, the bus for sending and receiving video or commands may be insulated or the case 1201 may include a designated space ensuring that none of the components contact the bus. Likewise, a wire or power conduit integrated within the case 1201 may communicate an electrical signal from the battery 1208 to the transceiver 1206, light 1204, and/or camera 1202. Alternatively, the electrical components may be serially connected in the positioned order for both powering the components and communicating a video signal (and command signals as needed).

A first end 1203 of the case 1201 may include or be formed of a lens or transparent plastic cover focusing or allowing light to be acquired as video content by the camera 1202. Any number of lenses may be utilized depending on the medical procedure being performed. For example, the lens may be a simple convex, biconvex, plano-convex, positive meniscus, negative meniscus, plano-concave, macro, zoom, apochromat, process, fisheye, stereoscopic, infrared, ultraviolet, swivel, biconcave, etc. lens. The lens may also be selected to prevent fluids from accumulating on the camera 1202 and light 1204 blocking the view of the relevant site.

In one embodiment, the camera 1202 is a condensed digital video camera configured for wirelessly communicating the video content through the transceiver 1206. The camera 1202 may be configured to capture video in response to the output of the light 1204, which may broadcast visible light, specific spectrums, infrared, ultrasound, ultra violet, x-ray, gamma ray, or other electromagnetic or non-electromagnetic imaging. In one embodiment, the light 1204 may be a fiber optic light that is powered by external sources. Any kind of digital or fiberoptic imaging or viewing device may be used. In one embodiment, the camera 1202 is a charge coupled device (CCD) camera, such as a CMOS camera composed of multiple stacked and interconnected semiconductor layers. The camera 1202 may be configured or selected to correspond to, pick-up, or capture the type of light 1204 inserted or installed in the portable endoscope 1200. The camera 1202 may be manually or remotely controllable. For example, the camera 1202 may include a swivel lens that rotates to give unique perspectives and camera angles. The lens or camera 1202 may be configured to protrude from or extend from the portable endoscope 1200. In another embodiment, the camera 1202 may be a fiber optic camera.

The camera 1202 may utilize any number of electronic or even vibrational spectra for chemical analysis, oximetry, disease classification, and molecular microscopy. For example, the camera 1202 may also be configured to include features of a microscope. In addition, diffuse reflection, fluorescence reflectance (fluorescence spectroscopy), Raman reflectance (Raman spectroscopy), and absorption may be observed, measured, or recorded by the camera 1202. The available or desired wavelength or spectrum may affect the light 1204 and camera 1202 selected for the portable endoscope 1200. The camera 1202 may be configured to produce 1-D spatial information utilizing a single wavelength or spectrum, 2-D spatial information utilizing wide-field spectroscopy/hyperspectral imaging, and 3-D spatial information utilizing tomography. The camera 1202 may be selected for a particular light 1204 or based on characteristics of the camera 1202 or generated video signal including resolution, intensity, frame rate, signal-to-noise ratio (SNR), peak SNR, noise immunity, timing, scanning, and so forth.

The video captured by the video camera may be transmitted directly or indirectly to the wireless device 1212 or computing device 1214. For example, the portable endoscope 1200 may communicate with the computing device 1214 through a network 1216. The network 1216 may utilize a communication standard, such as 802.11_ (e.g., 802.11n) as the standard continues to be updated. The direct or indirect communications may represent Bluetooth, ZigBee, WiFi, wireless local area network (WLAN), WiMAX, proprietary standards, or other radio frequency signals whether analog or digital that may be utilized to communicate a video signal. Any number of FCC, FDA, IEEE, ISO, CEN, ETSI, ARIB, ANSI, or IEC approved communications protocols or standards may also be transmitted by the transceiver 1206. Indeed, the types of wireless or wired standards or methods of communication are numerous.

The video signal may be received and displayed by the wireless device 1212 and/or computing device 1214 in real-time. The video signal may be formatted before or after being sent from the portable endoscope 1200. In one embodiment, the portable endoscope 1200 may include a processor, ASIC, FPGA, and/or other logic for managing the portable endoscope 1200 and processing the video signals. The video may be compressed in a raw or formatted state for communication by the transceiver 1206. For example, the video content may be packetized and communicated with or without encryption. Error detection and known packet analysis, processing, decryption, and other similar steps may be performed by a receiving device. In one embodiment, the portable endoscope 1200 may include a memory for storing the video content for subsequent analysis, review, documentation, training, or educational purposes. Alternatively, the video may be recorded by the wireless device 1212 or computing device 1214 for the same reasons. The wireless device 1212 and computing device 1214 may also act as a server to deliver or save content to any number of other client devices, systems, equipment, streaming configurations, or databases.

In another embodiment, a cable or wire may be utilized to communicate the video directly to the wireless device 1212, computing device 1214, or to an external transceiver that is not integrated with the case 1201 of the portable endoscope. (see, e.g., FIG. 16 below). The same cable may also be utilized to power the portable endoscope 1200 from a remote location further reducing the required size of the portable endoscope 1200. For example, a USB cable (e.g., standard, mini, micro, etc.) connected to the portable endoscope 1200 and wireless device 1212 may both power the portable endoscope 1200 and communicate video to the wireless device 1212.

A second end 1205 of the case 1201 may be removable for inserting or removing the components of the portable endoscope 1200. For example, the second end 1205 of the case 1201 may snap in, interconnect, latch, or include threads for securing the components of the case 1201. The portable endoscope 1200 may communicate with the wireless device 1212 or the computing device 1214.

In one embodiment, the components of the portable endoscope 1200 may be interchangeable. For example, even the relative positioning of components, such as the transceiver 1206 and battery 1208, may be varied. For example, the transceiver 1206 may more efficiently transmit and receive signals when positioned at the second end 1205 of the portable endoscope 1200 where the battery 1208 is shown. As a result, the portable endoscope 1200 may be configured for each patient or medical professional. For example, different cameras or batteries may be inserted into the case 1201 for different situations. In one embodiment, the video camera 1202 may be an infrared camera or spectrum-specific camera configured to view blood flow (or the lack thereof) within the nose. In another embodiment, the components of the portable endoscope 1200 are permanently connected.

In one embodiment, the components of the portable endoscope 1200 are powered by the battery 1208. The battery 1208 may be a high-powered energy storage device. For example, the battery 1208 may be a rechargeable or one-time use polymer battery, alkaline, zinc-air battery, lithium ion battery, thin film battery, ultrcapacitor, fuel cell, piezo electric generator, or other capacitors or batteries being developed and known in the art. The portable endoscope 1200 may be utilized repeatedly by replacing the battery 1208 as needed.

In another embodiment, the portable endoscope 1200 may include a port (not shown) for recharging the battery 1208 without removing the battery 1208 from the case 1201. Similarly, the portable endoscope 1200 may be configured to function in a wireless or wired state. For example, the portable endoscope 1200 may be connected directly to the computing device 1214 utilizing a cable, bus, wire, or connector, such as a micro-USB to USB connector for communicating video content. Additionally, the portable endoscope 1200 may not include the battery 1208 and instead may be powered and display video content through the wireless device 1212 or computing device 1214. For example, if the medical professional utilizes the wireless features of the portable endoscope draining the battery 1208, the portable endoscope 1200 may be connected to the computing device 1214 for the additional power requirements while simultaneously charging the battery 1208 for subsequent wireless usage. In another embodiment, the portable endoscope 1200 may be capable of being directly charged by, e.g., a wall outlet or other stationary or semi-stationary form of power supply.

In one embodiment, the camera 1202, light 1204, transceiver 1206, and battery 1208 may be interconnected by magnetic leads (not shown). The magnetic leads may automatically align and attach the components when placed in proximity to one another. The magnetic leads may include contacts for power, logic, or command signals, as well as video communications between each component. In another embodiment, leads, wires, contacts, or connectors may be built into the case 1201 for communicating power, video, control signals, or other signals between the camera 1202, transceiver 1206, and battery 1208 which may also include contacts or leads for interfacing with the case 1201. In another embodiment, the camera 1202, transceiver 1206, and battery 1208, and other described components may communicate signals utilizing ports, contacts, adapters, or male and female connectors. For example, the connectors may be a reduced size version of a mini-DIN, S-video, DVI, USB, coaxial, or HDMI connectors (micro video connectors). For example, the connectors may have a footprint of 0.25 mm-1 cm (diameter, area, length, etc), however, larger and smaller footprints are also possible. In addition, the diameter of the portable endoscope 1200 may vary between 0.1 mm and 1.5 cm with other sizes being produced for different applications.

The components of the portable endoscope 1200 may include longitudinal or lateral ridges, notches, or other alignment structures for properly aligning a component, such as the light 1204 and camera 1202 within the transceiver 1206 and battery 1208. For example, a ridge (not shown) along the top of the cylindrically-shaped camera 1202 may prevent the camera 1202 from being inserted in the light 1204 except when in the proper alignment. Similar ridges may be included on the light 1204, transceiver 1206, battery 1208, and logic if present. A corresponding notch or ridge on the case 1201 may align the components.

In another embodiment, portions or components of the portable endoscope 1200 may be separated by flexible connectors (not shown) (e.g., centipede configuration) that allow distinct components or portions of the portable endoscope 1200 to be individually angled and positioned. For example, wired connectors between each component of the portable endoscope 1200, such as a bus configured to communicate video signals and power, may enhance flexibility. For example, the light 1204 and camera 1202 portion of the portable endoscope 1200 may be angled a particular direction, relative to the remainder of the portable endoscope 1200, before insertion into the nose to view a selected sinus. The separated flexible portions of the portable endoscope 1200 may be manually adjusted or controlled by one or more servos. In one example, a mechanical pivot that provides resistive adjustments may be twisted to achieve the desired configuration of the portable endoscope. For example, a graphical user interface accessible through the computing device 1214 may be utilized to receive user selections or commands to pivot or rotate the portion of the portable endoscope 1200 including the camera 1202 and light 1204.

The electrical components of the portable endoscope 1200 may be manufactured utilizing processes for plastic, organic, and inorganic semiconductors, substrates, electronics, and logic. For example, the light 1204, transceiver 1206, battery 1208 may include flexible plastic-based substrates that function with printable conductive inks, organic light-emitting diode (OLED) layers and materials, and/or active-matrix thin-film-transistor arrays. Multilayer composite structures may be utilized to create and manufacture the portable endoscope 1200. For example, roll-to-roll processing with inkjet printing or spray deposition may be utilized to produce the flexible and reduced footprint components of the portable endoscope 1200. In one embodiment, the entire portable endoscope 1200 may be configured to flex to be moved and positioned to the correct location. Magnetic coupling, wires, and MEMs connections may be utilized to bend and flex the portable endoscope 1200.

FIG. 13 is a schematic, side-view of a light 1204 and camera 1202 in accordance with an illustrative embodiment. In one embodiment, the camera 1202 is cylindrically shaped and is inserted or partially encased in the light 1204. The light 1204 may be doughnut, or annular, shaped and configured to receive the camera 1202. During assembly of the various parts, the light 1204 and camera 1202 may be changed out as has previously been described.

In another embodiment, the camera 1202 and light 1204 may both be stacked or placed side by side. Alternatively, the camera 1202 and/or light 1204 may utilize different shapes, such as an ellipse, semi-circle, square, rectangle, or oval.

FIGS. 14 and 15 are schematic front views of the portable endoscope 1200 in accordance with illustrative embodiments. FIG. 14 illustrates the portable endoscope 1220 shaped as an oval. The light 1204 may be formed from boomerang-shaped lights. The light 1204 may emit a single spectrum of light or distinct spectra depending on the needs of the medical professional. For example, an upper portion 1206 of the light may be a miniaturized halogen light configured to emit a bright white light and the lower portion 1208 of the light may be an infrared LED that may be activated as needed. In one embodiment, the light 1204 and camera 1202 may directly abut each other. In another embodiment, any number of spacers or separators may be built into the case 1201, camera 1202, or light 1204 to correctly position the various components.

FIG. 15 illustrates the portable endoscope 1200 of FIG. 13 with a camera 1202 and a surrounding light 1204. The light 1204 may be a single light or may be composed of multiple lights that transmit light or signals at different frequencies or intensities. For example, different lights may be turned on at different times to examine cartilage, bone, blood flow, skin, or other forms of tissue. In one embodiment, the camera 1202 may fixedly or movably extend or protrude from the end of the portable endoscope 1200 to provide an uninhibited view of portions of the body during use.

In one embodiment, the camera 1202 may be connected to a motor that allows the camera 1202 to extend a small distance from the end of the portable endoscope 1200, rotate, and/or pivot. For example, the case 1201 may include bearings or rollers (not shown) for extending and rotating the camera 1202. The motor may be controlled remotely utilizing logic included in the portable endoscope 1200. For example, the wireless device 1212 of FIG. 12 may include a graphical user interface for rotating or pivoting the camera 1202, extending the camera 1202, switching between light spectrums, and recording video content. In addition, the camera 1202 may be able to zoom in and out. In one embodiment, the camera 1202 may utilize a fly eye configuration to get multiple views.

Figure 16:
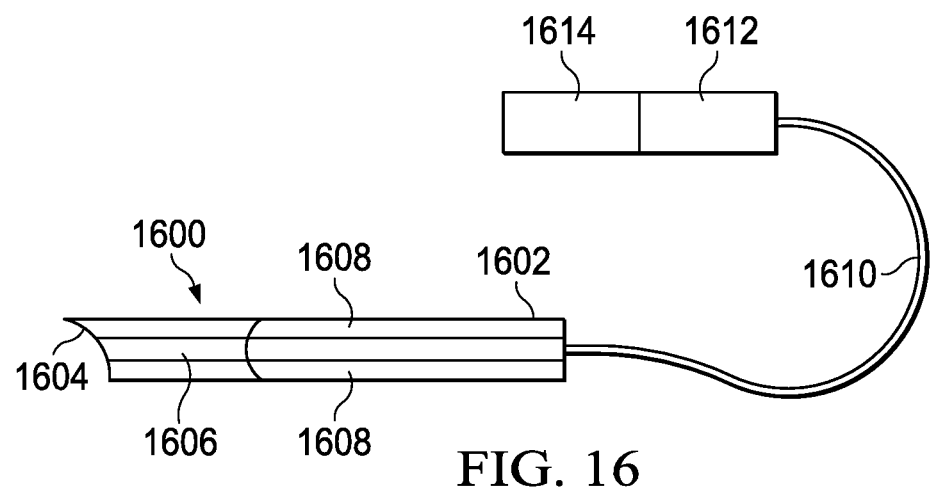
FIG. 16 is a schematic, pictorial representation of the portable endoscope in accordance with an illustrative embodiment.

FIG. 16 illustrates another embodiment of a portable endoscope 1600 in accordance with another embodiment. The portable endoscope 1600 may include a case 1602, first end 1604, camera 1606, light 1608, cable 1610, transceiver 1612, and battery 1614. The portable endoscope 1600 is externally connected to the transceiver 1612 and battery 1614. As a result, the size of the portable endoscope 1600 may be reduced even further.

In one embodiment, the cable 1610 of the portable endoscope 1600 is incorporated into an elastic, Velcro band, or securing component for the nasal guide. The cable 1610 may include a video cable for communicating a video signal to the transceiver 1612 as well as a wire for providing power. The transceiver 1612 and battery 1614 may be attached or integrated into the securing component (e.g., elastic band) of the nasal guide. For example, the Velcro band may include a pocket for inserting the transceiver 1612 and battery 1614, and the cable 1610 may be built in. In one embodiment, the transceiver 1612 may also include a port (not shown) for connecting the portable endoscope 1600 to a wireless device or computing device to view the video content and perform the medical procedure with the visual assistance of the portable endoscope 1600.

The first end 1604 of the portable endoscope 1600 may have a diagonal concave shape for preventing blood, mucous, pus, or other fluids from accumulating on the first end 1604 thereby blocking the view of the camera 1606 and the output of the light 1608. Blood that accumulates on the first end 1604 preferably runs to the bottom or side of the portable endoscope 1600 because of the shape.

In another embodiment, the first end 1604 may be rounded with an even concave shape that pushes or maintains an air bubble in front of the first end 1604 of the portable endoscope 1600 during utilization keeping the camera 1606 unobstructed.

Figure 17:
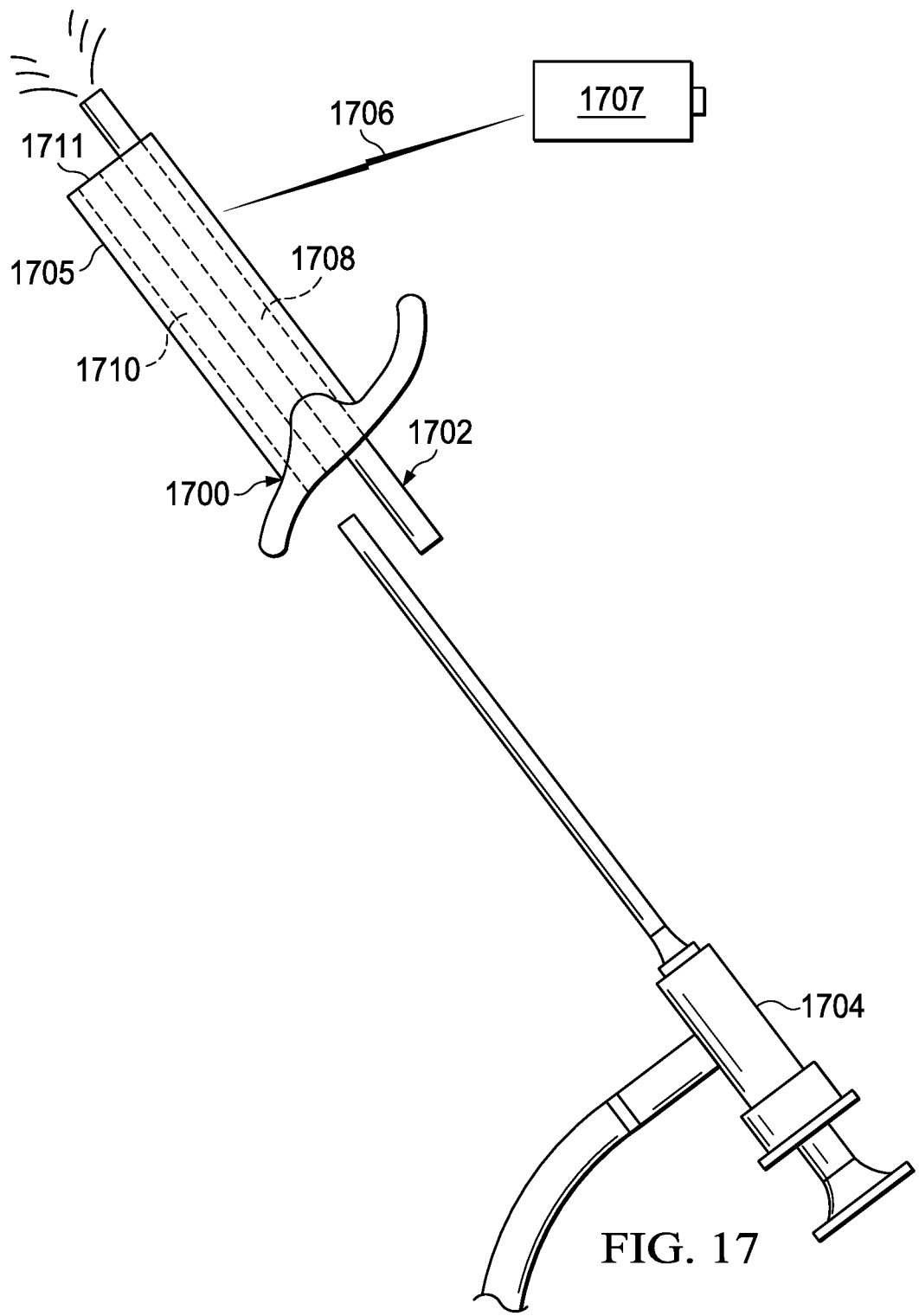
FIG. 17 is a schematic, pictorial representation of a nasal guide being utilized with a portable endoscope and a scope in accordance with an illustrative embodiment.

FIG. 17 is a schematic, pictorial representation of a nasal guide 1700 being utilized with a portable endoscope 1702 and a balloon catheter 1704 in accordance with an illustrative embodiment. The balloon catheter 1704 may be a medical device, endoscope, catheter, technology, or system, such as those sold by Acclarent. In one embodiment, the medical professional may insert and position the nasal guide 1700 in the nose of the patient as previously described. In this embodiment, the nasal guide 1700 includes an elongated frame 1705 enclosing a first lumen 1708 and a second lumen 1710. The lumens 1708 and 1710 of the nasal guide 1700 are elongated to reach further into the nasal cavity of the patient toward the sinuses for performing various medical procedures. As previously described, the elongated frame 1705 may narrow slightly at one end to facilitate expansion of the nostrils and to reach further into the nasal cavities as the nasal cavities narrow.

The portable endoscope 1702 and balloon catheter 1704 may be positioned in either the first lumen 1708 or the second lumen 1710 of the nasal guide 1700. In one embodiment, the nasal guide 1700 may include the first lumen 1708 and second lumen 1710 for both nostrils and the portable endoscope 1702 and balloon catheter 1704 may be moved between any of those lumens based on the physical condition of the patient, medical procedure being performed, and/or preferences of the medical professional.

Next, the portable endoscope 1702 may be inserted through the first lumen 1708 of the nasal guide 1700 to the nasal cavity of the patient. The portable endoscope 1702 may be turned on and activated to begin communicating video through a wireless signal 1706 to a wireless adapter 1707 wireless device, or computing device as previously described. The wireless adapter 1707 may be utilized with any number of electronic devices to receive or format the video content in real-time. In one embodiment, the wireless adapter 1707 is an adapter, such as a USB adapter, dongle, or other interface configured to receive wireless communications from the portable endoscope 1702, and may decode, decrypt, and/or format the video signal retrieved by the camera of the portable endoscope 1702 for view by a medical professional or other party.

The portable endoscope 1702 is secured by the nasal guide 1700 at a desired position and location selected by the medical professional. The portable endoscope 1702 may easily be further inserted, removed, or rotated. The video provided by the portable endoscope 1702 may be communicated to one or more other devices for guiding or informing the medical professional while performing a medical procedure. The portable endoscope 1702 may provide both light and video within the nasal or body cavity or other orifice. The light and video may be utilized to position and utilize the balloon catheter 1704. For example, the video from the portable endoscope 1702 may ensure that a wire and balloon inserted through the balloon catheter are guided into a selected sinus for performing a procedure, such as balloon sinuplasty.

In another embodiment, the portable endoscope 1702 may include a motorized end for controlling the positioning of the inserted end with the light and camera. For example, the portable endoscope 1702 may pivot 90° and rotate 360°. In addition, the light and camera may be configured to be extended or retracted from the frame of the portable endoscope 1702. For example, a graphical user interface of an iPad, tablet, or other computing device may be utilized to vertically and horizontally position and angle the portable endoscope (and corresponding light and camera) to a desired position to illuminate tissue and provide video guidance of the balloon catheter 1704 and insertion of a wired balloon into one or more sinuses.

In another embodiment, the first lumen 1708 or the second lumen 1710 may be enclosed or sealed on an interior end 1711. As a result, a non-medical scope, borescope, probe, or other instrument may be inserted into the nasal guide 1700 without requiring an FDA approved device or extensive sanitation. The sealed end of the lumen may be formed of a transparent glass or plastic for videoing through the nasal guide 1700. In another embodiment, the nasal guide 1700 includes extensions (not shown) sized only slightly bigger than the first lumen 1708 or second lumen 1710 for extending the reach of the openings. The extensions may be straw-like extensions that further extend the reach of the nasal guide 1700 and may be open ended or enclosed. Depending on the configuration of the nasal guide 1700 as has been illustrated in the previous embodiments, the extensions may extend from 1 cm to 20 cm from the end of the elongated frame 1705, but the distance may vary from this depending on the procedure or application.

In another embodiment, the extensions or the elongated frame 1705 of the nasal guide 1700 may include corrugations (not shown) like a flexible straw for angling or positioning the first lumen 1708 and second lumen 1710. For example, the nasal guide 1700 may be manually bent or configured particularly at the corrugations to enhance performance of the medical procedure and the nose of the patient. Similarly, a portion of the frame 1705 of the portable endoscope 1702 may be corrugated for manually, mechanically, or electrically configuring the shape and direction of the portable endoscope 1702.

Figure 18:
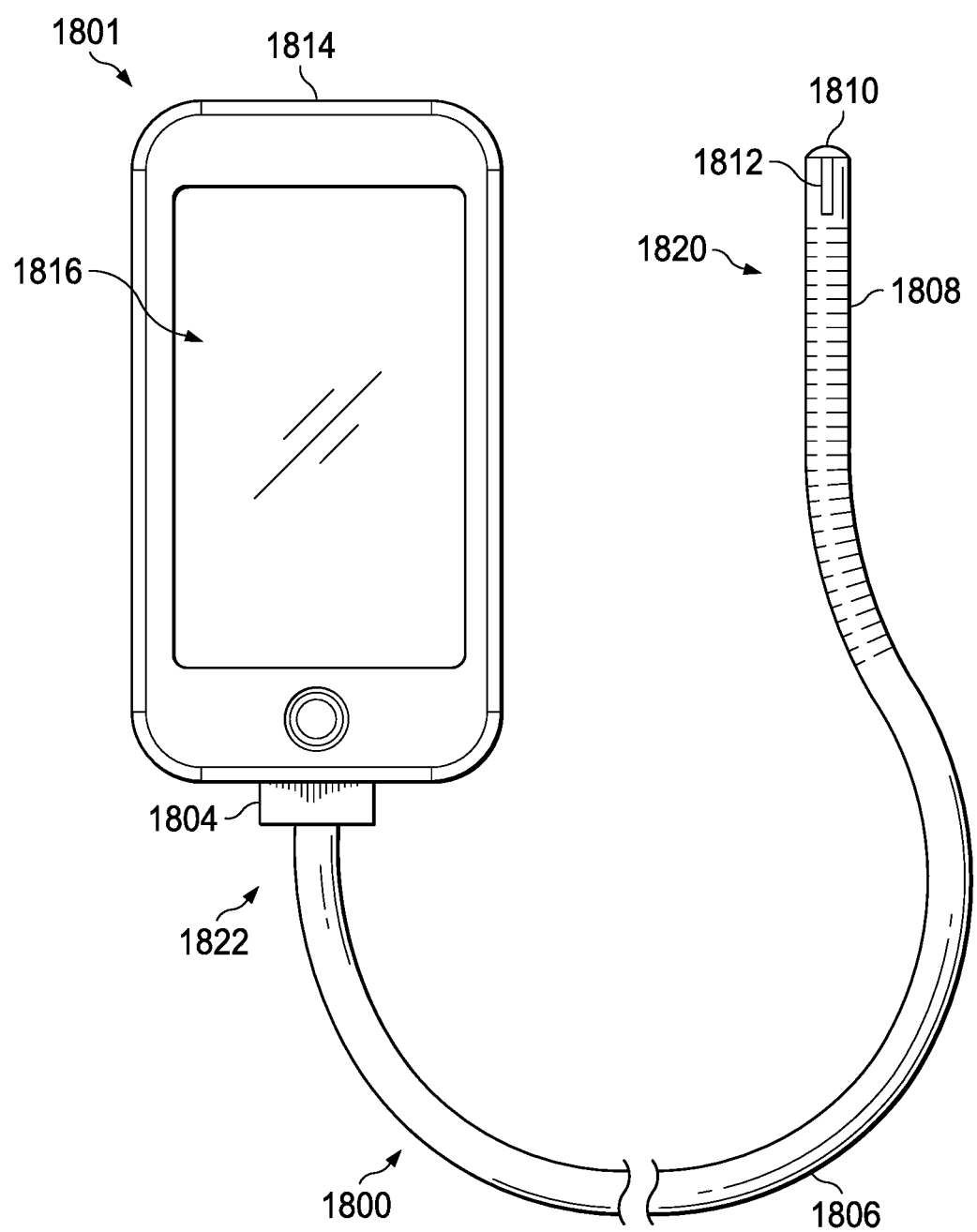
FIG. 18 is a schematic, pictorial representation of an endoscopic peripheral in accordance with an illustrative embodiment.

FIG. 18 is a schematic, pictorial representation of an endoscopic peripheral 1800 in accordance with an illustrative embodiment. In one embodiment, the endoscopic peripheral 1800 is part of an endoscopic system 1801. The endoscopic system 1801 may be utilized to illuminate, capture, view, and manage captured content. The endoscopic system 1801 may be utilized for self-examination or to examine others based on the circumstances.

The endoscopic system 1801 may be sold to individual users for performing self-examinations or examinations of others. For example, users in remote locations, such as rural users, military users, campers, or so forth, may utilize the endoscopic system 1801 to do examinations, perform analysis, or so forth. The endoscopic system 1801 may also be utilized to perform an after-hours examination or an examination based on specific instructions from a medical professional. In one embodiment, the endoscopic peripheral 1800 may be configured to automatically display, store, and communicate content.

In one embodiment, the endoscopic system 1801 includes a plug 1804, a flexible cord 1806, a bending portion 1808, a camera 1810, a light 1812, a wireless device 1814, and an application 1816. The camera 1810, the light 1812, and the bending portion 1808 may also be referred to as a first end 1820 and the plug 1804 and/or a portion of the flexible cord 1806 may also be referred to as a second end 1822. In one embodiment, all or portions of the endoscopic peripheral 1800 may be replaceable or interchangeable. For example, the bending portion 1808 may be replaced with a straight fixed or straight curved end for visualizing a patient's throat or nose. The first end 1820 or the second end 1822 may also be replaced due to damage. In one embodiment, the endoscopic peripheral 1800 may include plugs or interfaces separating the first end 1820 and second end 1822 from the flexible cord 1806.

The endoscopic peripheral 1800 may include a fixed or rigid housing or case for encompassing the enclosed components and connections, such as those describe in the first end 1820. In another embodiment, the components of the endoscopic peripheral 1800 are integrated, fit together, or adhered. In yet another embodiment, the components of the endoscopic peripheral 1800 are substantially enclosed by an exterior covering or surface of the flexible cord 1806. All of the components of the camera 1810 and light 1812 are not covered to maintain the necessary functionality as is described herein.

The plug 1804 may be embodied in any number of configurations. For example, the plug 1804 may represent any number of standardized or proprietary connectors. The plug 1804 may include any number of pins or contacts for interfacing with electronic devices. Wires, paths, connectors, or conductors within the flexible cord 1806 may communicate the captured video content to the plug 1804 for communication to an interconnected electronic device, such as the wireless device 1814.

In another embodiment, the plug 1804 may be plugged into an adapter (not shown) that may be directly connected to the applicable computing or communications device. The adapter may be especially useful for situations where the flexible cord 1806 is not long enough. For example, the plug 1804 may be a USB plug (e.g., USB 1.x, 2.x, 3.x, 4.x, type A, B, etc), and the adapter may be configured to adapt the USB connection to other plug interfaces, such as a standard USB (Type A, B), micro-USB, mini USB, USB On-The-Go, lighting, Apple connectors, or so forth. However, the plug 1804 may be any standard (e.g., GSMA trade association approved) or proprietary plug for communicating with computing or communications devices provided by known manufacturers and service providers (e.g., Apple, Samsung, RIM, Qualcomm, ZTE, LG, Amazon, Huawei, Google, HTC, Nokia, Microsoft, Sony Ericcson, Dell, Acer, Lenovo, NEC, Kyocera, Mitsubishi, Panasonic, Sanyo, Sharp, Alcatel, Toshiba, etc). In another embodiment, the adapter may be a wireless transceiver for communicating with the wireless device 1814 or a computing device through a wireless connection, such as Bluetooth, Wi-Fi, Zigbee, near field communication (NFC), WiMAX, PCS, GSM, CDMA, GPRS, infrared, a proprietary connection, or so forth. Any number of FCC, FDA, IEEE, ISO, CEN, ETSI, ARIB, ANSI, or IEC approved wireless communications protocols or standards may also be transmitted by the endoscopic peripheral 1800 or the adapter. The wireless adapter may also include logic for encoding, formatting, and processing signals to and from the wireless device 1814. The wireless adapter may be utilized for applications where the standard cord length is insufficient or the environment is otherwise incompatible.

The length of the flexible cord 1806 may vary based on the application. For example, the flexible cord 1806 may vary between 6 cm to 5 meter in length. The endoscopic peripheral 1800 may also be utilized with a repeating or extension device to extend the length of the flexible cord 1806. In one embodiment, the flexible cord 1806 shields and protects the twisted pairs, wires, or cabling encompassed within the endoscopic peripheral 1800. The exterior of the flexible cord 1806 may be composed of plastic, rubber, or another protecting material. For example, the flexible cord 1806 may represent medical grade plastic that may be more easily cleaned and sterilized for repeated use. In one embodiment, the flexible cord 1806 may include an outer protective layer, a shield (or shielding), an electrostatic shield, insulation, and one or more conductors or electrical contacts configured to communicate power, image content, and control signals. For example, the electrostatic shield may a jacketed wire mesh configured to reduce electronic noise and interference.

The bending portion 1808 is configured to be bent or positioned and thereafter hold the position. For example, the user may position the bending portion 1808 as an arced shape that may facilitate looking into the mouth of an individual. In one embodiment, the bending portion 1808 may be linked to controls (not shown) or a motor (not shown) for controlling the motion, angle, or position of the bending portion. For example, a directional controller may be configured to move the camera 1810 and light 1812 to a particular direction, position, or angle. In another embodiment, the bending portion 1808 may be flexible enough to deform based on the provided space and configuration in which the endoscopic peripheral 1800 is being utilized.

The camera 1810 may be a video or still image capturing device as was previously described. In one embodiment, the camera 1810 is a miniaturized camera inserted in the tip of the endoscopic peripheral 1800 and configured to communicate the captured content through a wire, bus, cable or so forth. In one embodiment, the camera 1810 may include a processor, DSP, ASIC, graphics rendering chip, or other processing unit or circuit for processing the captured images. In another embodiment, the camera 1810 may communicate the raw captured content to a separate electronic device for processing. The camera 1810 may also represent a fiber optic camera with processing components at the second end 1822 near or integrated with the plug 1804.

In one embodiment, the endoscopic peripheral 1800 may include an integrated or externally connected thermometer (not shown). For example, the camera 1810, light 1812, or bending portion 1808 may include an integrated thermometer (not shown). The thermometer may be a digital thermometer utilized to accurately determine a user's temperature and display the information to the wireless device 1814. However, the thermometer may be a mercury-in-glass thermometer, infrared thermometer, or liquid crystal thermometer that may be utilized to check temperature as well as determine whether an individual has a fever or is hypothermic.

The described embodiments of the endoscopic peripheral 1800 and wireless endoscope are configured to be universal plug-and-play devices for both computing, communications, and other electronic devices. In one embodiment, the endoscopic peripheral 1800 is hot pluggable and configured for zero configuration connections. For example, when physically or wirelessly connected to an electronic device, the endoscopic peripheral 1800 or wireless endoscope may automatically establish working configurations with other devices, such as computing, communications, or other electronic devices. The plug-and-play standards comply with applicable wired or wireless standards set by the Universal Plug and Play (UPnP), ISO, IEEE (e.g. 802.11X, 802.14X, DICOM, MIB, Personal Health Data (PHD), and so forth. Combined standards or proprietary standards may also be utilized.

In another embodiment, the wireless device 1814 (or a computing device) may include a processor, memory, and other hardware, firmware, and software that are specifically designed to interoperate with the endoscopic peripheral 1800. The endoscopic peripheral 1800 may also include a processor and memory. The processor is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks. For example, the processor may perform encoding of standard or high definition content captured by the camera 1810 to reduce latency when communicating or viewing the content. In another example, the content may be raw, encoded, or formatted content that is processed by the interconnected electronic device, such as the wireless device 1814.

The processor may be a single chip or integrated with other computing or communications elements. The memory may be a hardware element, device, or recording media configured to store data for subsequent retrieval or access at a later time. The memory may be static or dynamic memory. The memory may include a hard disk, random access memory, cache, removable media drive, mass storage, or configuration suitable as storage for data, instructions, and information. In one embodiment, the memory and processor may be integrated. The memory may use any type of volatile or non-volatile storage techniques and mediums.

In one embodiment, the endoscopic peripheral 1800 may include a memory to store content captured by the camera 1810. For example, each new examination session may be saved as a discrete file that may be communicated, accessed, or retrieved later. The memory may also store an application that is utilized to interface the endoscopic peripheral 1800 with the wireless device 1814. For example, a program, script, sub-routine, set of instructions, or so forth may be stored in the memory so that when the endoscopic peripheral is plugged into an electronic device, the electronic device is configured to decode, process, format, and view the captured content as well as manage functionality of the endoscopic peripheral 1800. The user may utilize the wireless device 1814 to turn the endoscopic peripheral 1800 on and off, adjust the light intensity, resolution, video/image characteristics (e.g., compression, format, brightness, contrast, frames, aspect ratio, etc), physically angle the camera or lights, adjust or turn on and off different sets of lights, automatically stream content, store content on the endoscopic peripheral 1800, wireless device 1814, or other component The wireless device 1814 may include any number of hard keys or soft keys. The hard keys are dedicated buttons or interface elements hard-coded for a single, unique, and consistent purpose. Examples of hard keys include the 12-buttons of the traditional alpha-numeric keypad, the send/end keys commonly found on mobile phones, and buttons to initiate or end a speakerphone function. The soft keys are programmable buttons or interface elements. Soft keys are usually located alongside a display device and may perform different functions dependent on the text shown near the soft keys on the display. Examples of soft keys may include a power button for the endoscopic peripheral 1800.

The wireless device 1814 may include any number of computing and telecommunications components, devices or elements which may include busses, motherboards, circuits, ports, interfaces, cards, converters, adapters, connections, transceivers, displays, antennas, and other similar components. For example, the wireless device 1814 may represent a voice over Internet protocol (VoIP) phone, plain old telephone system (POTS) telephone, e-reader, or so forth that may receive and/or communicate the content captured by the camera 1810.

In one embodiment, the content captured by the endoscopic peripheral 1800 may be communicated to, through, or by a portal or other software or hardware interface. The portal may be a web site that functions as a central point of access to information on the Internet or an intranet. The portal may be accessed from any computing or communications system or device enabled to communicate through a network connection. The endoscopic peripheral 1800 may have a hardware or software identifier that is utilized to automatically route captured content to the portal for viewing, storage, management, or so forth.

Figure 19:
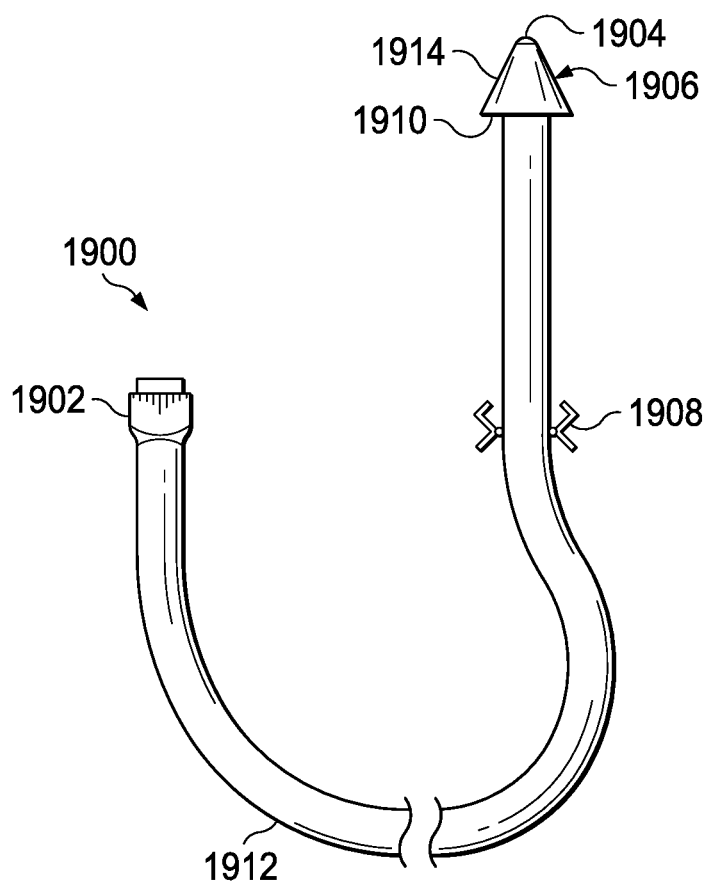
FIG. 19 is a schematic, pictorial representation of another endoscopic peripheral in accordance with an illustrative embodiment.

FIG. 19 is a schematic, pictorial representation of another endoscopic peripheral 1900 in accordance with an illustrative embodiment. The endoscopic peripheral 1900 may include a micro USB plug 1902, a camera 1904, a funnel shaped head 1906, and a latch 1908.

In one embodiment, the endoscopic peripheral 1900 may include a micro USB plug 1902. The micro USB plug 1902 may be configured to be inserted into a computing or communications device. For example, many smart phones include micro USB connectors that may be configured to communicate with the endoscopic peripheral 1900. However, the micro USB plug 1902 may be replaced by any miniaturized plug whether standardized or custom designed. The endoscopic peripheral 1900 may also include as a standard accessory one or more adapters for converting the plug, such as the micro USB plug 1902, to a different standard or format, such as USB.

In another embodiment, the adapter (not shown) may be a wireless transceiver. The wireless transceiver adapter may include a rechargeable battery and may be configured to communicate with computing or communications devices utilizing Bluetooth, Wi-Fi, near field communications, Zigby or other communications standards, protocols, or formats.

In one embodiment, a body 1912 of the endoscopic peripheral 1900 may include any number of strengthening, shielding, or strength components. For example, the body 1902 or cord portion of the endoscopic peripheral 1900 may include a wire or plastic framework both surrounding and shielding the wires within the body 1912. As a result, the body 1912 may be shielded from radio frequency signals and other electronic noise that are common in the various environments in which the endoscopic peripheral 1900 will be utilized. In addition, the structure of the body 1912 may prevent the body 1912 from stretching, tearing, or sustaining excess wear due to repositioning or otherwise moving the endoscopic peripheral 1900. For example, the body 1912 may be long enough that a medical professional may occasionally step on or run over the body 1912 with an office chair or otherwise apply pressure and strain on the endoscopic peripheral 1900 which it is configured to bear without losing functionality.

In one embodiment, the endoscopic peripheral 1900 may include the funnel shaped head 1906. The camera 1904 may be placed at the tip of the funnel shaped head 1906 for visualizing a patient's ear, nose, or other organ or body portion. The funnel shaped head 1906 may be configured as a safety structure for the endoscopic peripheral 1900. For example, the increased angle and widening head of the funnel shaped head 1906 may ensure that a user does not insert the endoscopic peripheral 1900 too far into a patient's body. For example, the funnel shaped head 1906 may prevent the user from damaging a patient's eardrum when trying to visualize a potential medical issue in the patient's ear. In three-dimensions, the funnel shaped head 1906 is conically shaped with the camera 1904 at the tip of the head. The length and angles of the funnel shaped head 1906 may vary. For example, the funnel shaped head 1906 may be elongated for viewing the sinuses of a patient or may be shorter for viewing the ear of a patient.

In one embodiment, sides 1914 of the funnel shaped head 1906 may be curved or arced to select an insertion depth for the funnel shaped head 1906 within the patient. The funnel shaped head 1906 and the camera 1904 may be replaceable or attached to the body 1912 for customization. For example, the shape and size of the funnel shaped head 1906 may vary for pediatric, adult, and animal usage. For example, the funnel shaped head 1906 may be very short in length and wide for visualizing children's eardrums when compared with a funnel shaped head 1906 that may be utilized to visualize the sinuses of a horse.

In another embodiment, the ends 1910 of the funnel shaped head 1906 may include extensions or a collar that are integrated with or attached to the funnel shaped head 1906 at the ends 1910 to prevent over-insertion or extension of the endoscopic peripheral 1900 in the patient's body during utilization. The endoscopic peripheral 1900 may include one or more latches 1908 for securing a disposable cover (not shown). For example, the latch 1908 may be configured to hold a securing ring 2006 (shown in FIG. 20 below).

In another embodiment, the latch 1908 may be one or more hooks or extensions hingedly or pivotally attached to the body 1912 to secure or receive the securing ring of the disposable cover. The latch 1908 may also include a release for removing the disposable cover from the latch 1908. As a result, the disposable cover is secured in place during utilization and easily attached and removed when working with a number of patients, such as in the clinical or emergency setting. As previously disclosed, the funnel shaped head 1906 ending may be flexible for varying applications. For example, the funnel shaped head 1906 may be formed of a flexible plastic or rubber material that is less likely to injure a patient during a rigorous examination. The disposable cover may also include a swabbing section for swabbing a body part for analysis (e.g., swabbing the users nasal pages, tonsils, throat, cheek, etc). The swabbing section may be formed of an absorbent material, such as a polyster knit fabric, adhered or integrated with the disposable cover.

Figure 20:
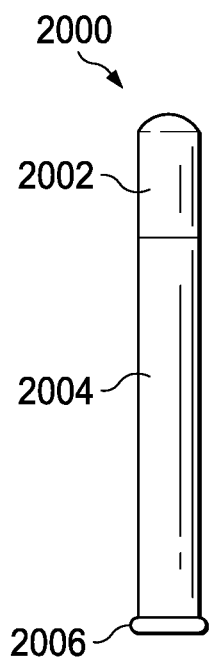
FIG. 20 is a schematic, pictorial representation of a disposable cover for an endoscopic peripheral in accordance with an illustrative embodiment.

FIG. 20 is a schematic, pictorial representation of a disposable cover 2000 for an endoscopic peripheral in accordance with an illustrative embodiment. The disposable cover 2000 may be utilized for any number of medical or surgical instruments or for other devices, systems, and applications. For example, the disposable cover 2000 may be utilized on a borescope in a clean room of a semiconductor manufacturing facility. In one embodiment, the disposable cover 2000 includes a rigid portion 2002, a flexible portion 2004, and a securing ring 2006.

In one embodiment, the disposable cover 2000 includes two or more sections or portions including at least the rigid portion 2002 and the flexible portion 2004. In other embodiments, the disposable cover 2000 may be formed entirely of rigid or flexible materials corresponding to the rigid portion 2002 and the flexible portion 2004, respectively.

The rigid portion 2002 may be composed of a clear material for enabling a camera of the endoscopic peripheral to gather image and video content. The rigid portion 2002 may also include a built-in lens for viewing an area at the viewing end for enhancing the images captured by the camera. For example, the rigid portion 2002 may be formed of a clear plastic, such as a U.S. Pharmacopeia (USP) Class V and VI silicon, rubber, polymers, or plastic materials (or a combination thereof).

In one embodiment, the flexible portion 2004 may composed of latex, Vytex, resin (e.g., AT-10 resin) plastic, polyurethane, polyisoprene, nitrile, or so forth. The flexible portion 2004 may allow the disposable cover 2000 to bend, flex, or deform with the motion of the endoscopic peripheral. For example, the endoscopic peripheral may be configured to bend as much as 90-360°. The disposable cover 2000 may flex with the endoscopic peripheral to protect the patient (e.g., tissues, membranes, organs, blood, etc.) and prevent contamination of the endoscopic peripheral.

The rigid portion 2002 and the flexible portion 2004 may be connected or bonded in any number of ways. In one embodiment, the flexible portion 2004 is crimped within an end of the rigid portion 2002. In another embodiment, the rigid portion 2002 is heat bonded to the flexible portion 2004. In another embodiment, the rigid portion 2002 and flexible portion 2004 are adhered or welded to one another.

In another embodiment, the disposable cover 2000 may be formed of a rigid plastic material. A rigid cover may be particularly useful for embodiments of the endoscopic peripheral that are rigid or otherwise fixed.

Figure 21:
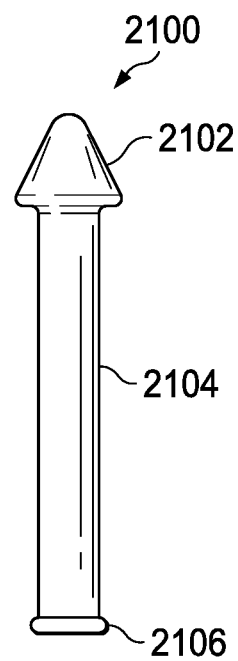
FIG. 21 is a schematic, pictorial representation of a disposable cover for the endoscopic peripherals in accordance with an illustrative embodiment.

FIG. 21 is a schematic, pictorial representation of a disposable cover 2100 for the endoscopic peripherals in accordance with an illustrative embodiment. In one embodiment, the disposable cover 2100 of FIG. 21 may be configured to be utilized with the endoscopic peripheral 1900 of FIG. 19. The head portion 2102 may be configured to be positioned over the funnel shaped head. Similarly, the shaft portion 2104 may be flexible and expandable allowing the disposable cover 2100 to be pulled over the funnel shaped head. In one embodiment, the securing ring 2106 may be expanded to fit over the funnel shaped head when being positioned. For example, the securing ring 2106 may include a broken or split section allowing the securing ring 2106 to deform or open to receive the funnel shaped head 1906.

In another embodiment, the securing ring 2106 may be a fortified section of the disposable cover 2100. For example, the material making up the disposable cover 2100 may be formed (e.g., compressed, molded, extruded, shaped, etc.) into a substantive solid ring forming the securing ring. The disposable cover 2100 may include one or more reinforced holes (not shown) for attaching to one or more latches, hooks, or extensions of the endoscopic peripheral 1900. The disposable cover 2100 may define the fortified holes, such that the disposable cover 2100 does not rip, tear, rupture, or break during utilization, placement, or so forth.

In alternative embodiments, the securing ring 2106 may be configured to actively secure the disposable cover 2100 to the endoscopic peripheral 1900, surgical device, medical instrument, or other tool. For example, the securing ring 2106 may be configured as a miniaturized wire tie, drawing strings, buckle, or clamp. The securing ring 2106 may be formed of a non-slip material that allows it to be tightly drawn against the endoscopic peripheral 1900 or other device without slipping during utilization. As a result, the securing ring 2106 may be easily unlatched, unbuckled, or cut when its purpose is fulfilled and needs to be disposed of. The disposable cover 2100 may be a stand-alone embodiment for utilization with a number of different devices and tools. The size (e.g. length, diameter, etc) and shape (e.g., circular, square, or oblong cross sections, differently sized head, body, and end, etc.) of the disposable cover 2100 may correspond to the medical device or tool as is herein described.

Figure 22:
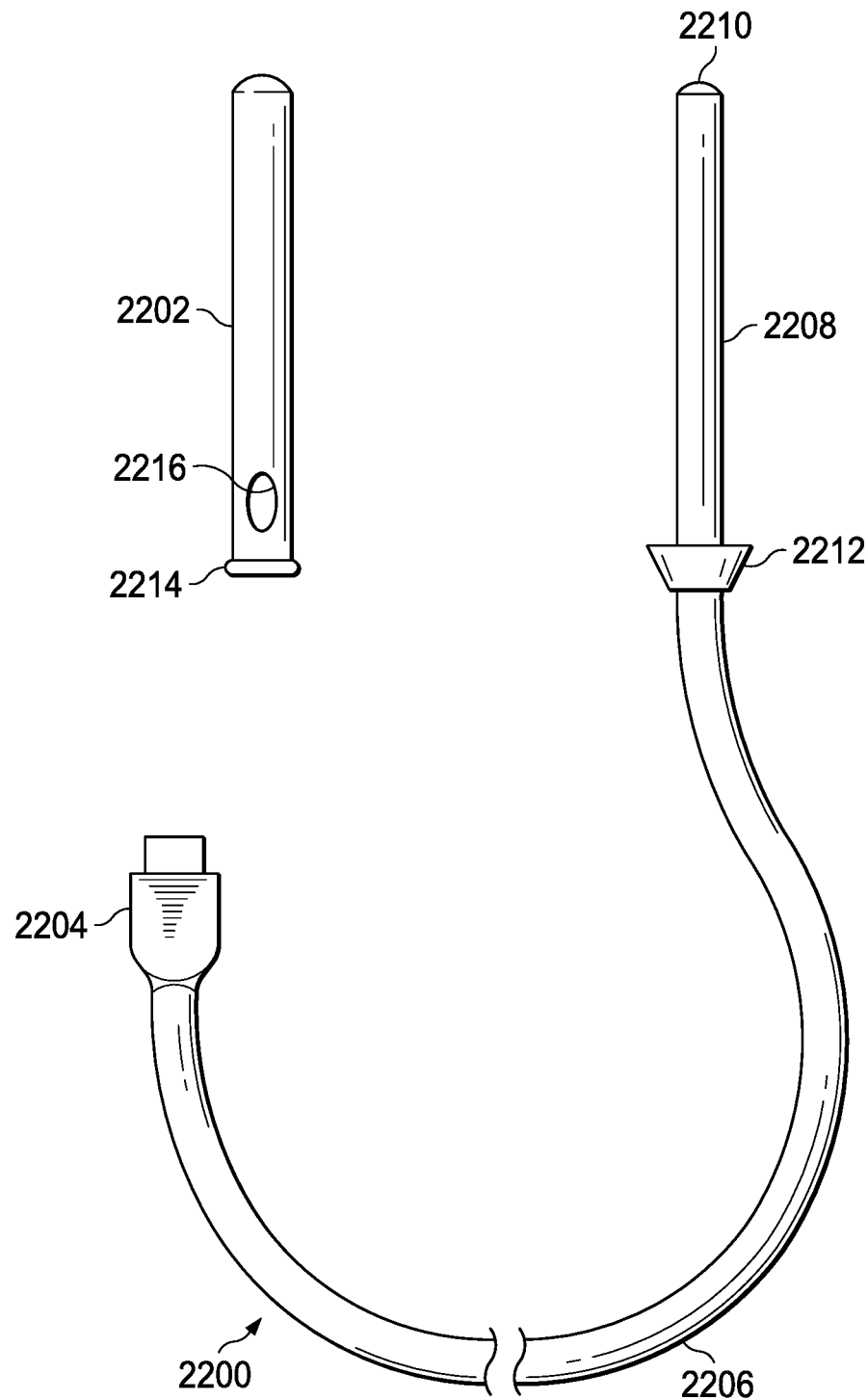
FIG. 22 is a schematic, pictorial representation of a plug-and-play endoscopic peripheral and a cover in accordance with an illustrative embodiment.

FIG. 22 is a schematic, pictorial representation of a plug-and-play endoscopic peripheral 2200 and a cover 2202 in accordance with an illustrative embodiment. The endoscopic peripheral 2200 may include a plug 2204, a body 2206, a head 2208, a camera 2210, and a clamp 2212.

In one embodiment, the plug 2204 is a USB or other plug-and-play connector. As a result, the endoscopic peripheral 2200 may not require a special device driver or support software. For example, the implementation the USB plug (e.g., USB 2.0, 3.0, 4.0, etc), Ethernet, FireWire, or other plug-and-play standard may allow the endoscopic peripheral 2200 to be automatically recognized by computing or communications devices. The plug 2204 may also be a proprietary connector, such as a connector for Apple devices (e.g., lightning, etc.). This may be particularly useful for users that have limited experience with electronic devices, such as computers.

In one embodiment, the endoscopic peripheral 2200 may be automatically powered on and activated in response to the plug 2204 being connected to an electronic device, such as a computer or a cell phone. The endoscopic peripheral 2200 may also include a switch, button, or other selection component for performing any of: powering on/off the endoscopic peripheral 2200, increasing or decreasing the light intensity, changing from video to still images, changing light spectra, adjusting resolution, adjusting video or camera settings, or so forth.

As previously disclosed, the head 2208 of the endoscopic peripheral 2200 may be fixed or flexible. In one embodiment, the head 2208, including the clamp 2212, may be removably attached to the body 2206 of the endoscopic peripheral 2200. The endoscopic peripheral 2200 may be configured to receive fixed or flexible heads depending on the medical application. The disposable cover 2202 may similarly be fixed or flexible based on the configuration of the head 2208.

The clamp 2212 is configured to secure the disposable cover 2202 tightly against the head 2208 and the camera 2210. The clamp 2212 may secure an end or securing ring 2214 of the disposable cover 2202. The disposable cover 2202 may also include a hole 2216. The hole 2216 is a receptacle or attachment point. The hole 2216 is defined by the disposable cover 2202 and may be utilized to secure disposable cover during utilization.

Figure 23:
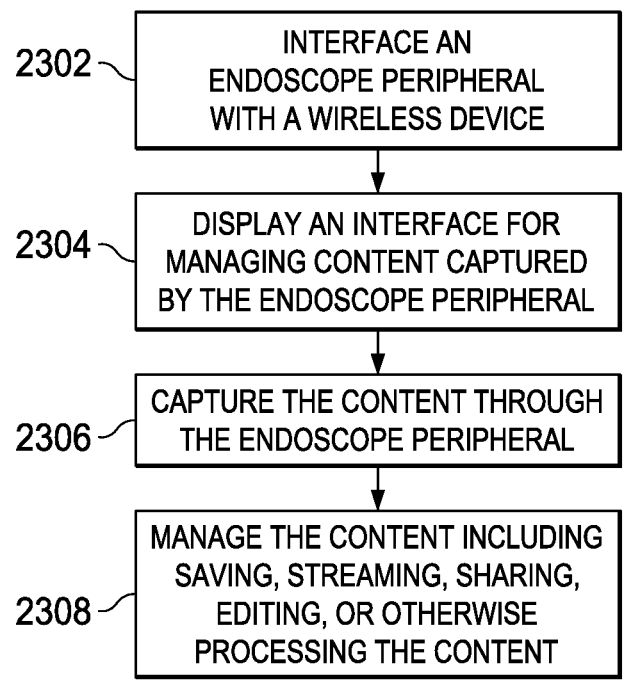
FIG. 23 is a flowchart of a process for utilizing an endoscopic peripheral in accordance with an illustrative embodiment.

FIG. 23 is a flowchart of a process for utilizing an endoscopic peripheral in accordance with an illustrative embodiment. In one embodiment, the process of FIG. 23 may be implemented by a system controlled by a user utilizing an endoscopic peripheral with a computer or wireless device (utilized for purposes of simplicity). The endoscopic peripheral may include a head that is covered with a disposable cover or otherwise sanitized before being utilized.

The process may begin by interfacing an endoscopic peripheral with a wireless device (step 2302). For example, the user may have inserted a port end of the endoscopic peripheral in a computer or wireless device for capturing the images. In one embodiment, the endoscopic peripheral may be powered by the computer or wireless device. In another embodiment, the endoscopic peripheral may include a separate power supply, such as batteries or AC/DC power plug. The image content may also be communicated from a camera of the endoscopic peripheral to the computer or wireless device to be viewed, processed, or saved. The endoscopic peripheral may also perform some image processing, filtering, noise reduction, formatting, clean up, and other similar operations before communicating the captured content to the computer or wireless device.

Next, the system displays an interface for managing content captured by the endoscopic peripheral (step 2304). In one embodiment, the interface is a program, application, or other graphical user interface that is activated in response to user input (e.g., opening an application, selecting an icon, etc) or in response to the connector/plug end of the endoscopic peripheral being inserted in the computer or wireless device.

Next the system captures the content through the endoscopic peripheral (step 2306). The content of step 2306 may include video and image content in any number of spectra. The endoscopic peripheral may include one or more LEDs, fiber optics, or other light sources to enable the camera of the endoscopic peripheral to fully capture the desired content.

Next, the system manages the content including saving, streaming, sharing, editing, or otherwise processing the content (step 2308). In one embodiment, the interface is a graphical user interface that provides the user with managing and processing options, such as record the content, upload the content, send or share the content with a designated user, contact or device, stream the content to a designated user, device, or location in real-time, or edit the content. The software utilized with the endoscopic peripheral may be standard or default software utilized by a computing or communications device or proprietary software that is automatically or manually installed in response to connecting the endoscopic peripheral for the first time. The content may be stored and then uploaded to a designated location specified by the user or associated with the endoscopic peripheral. For example, video content captured by the endoscopic peripheral may be automatically uploaded to a server/database through one or more networks and then saved under an identifier associated with the endoscopic peripheral. For example, a serial number may be associated with a patient identifier. As a result, users in remote locations or at home may be able to be treated by doctors even if they do the examination themselves.

Figure 24:
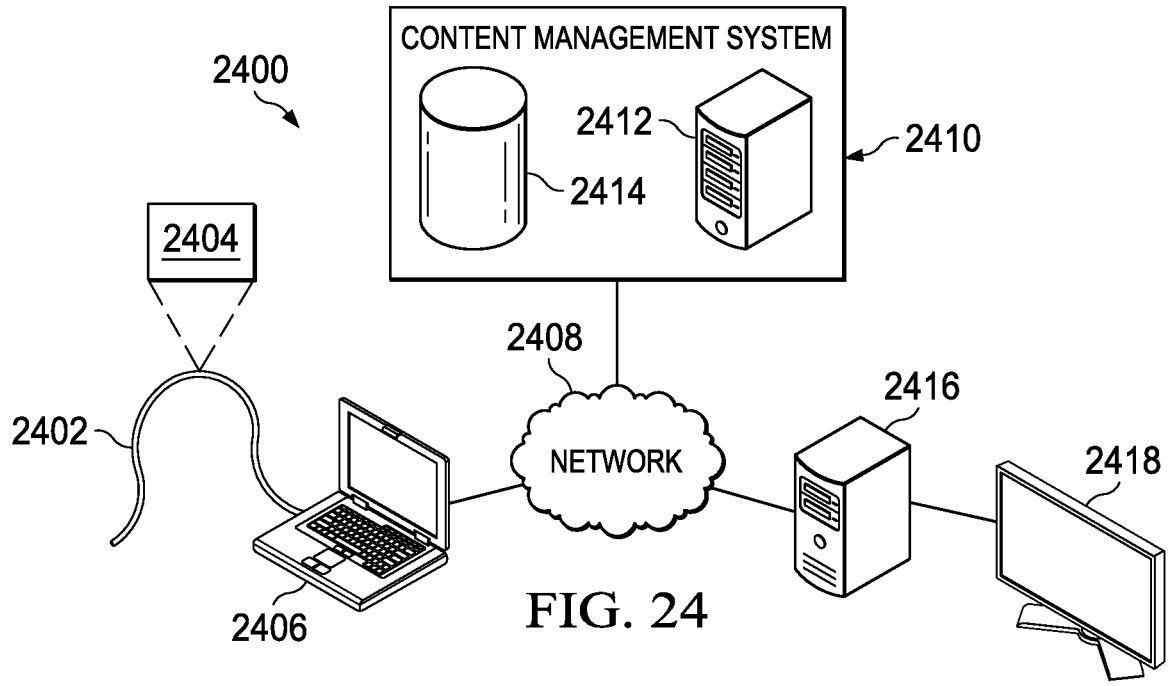
FIG. 24 is a schematic, pictorial representation of a communications environment in accordance with an illustrative embodiment.

FIG. 24 is a schematic, pictorial representation of a communications environment 2400 in accordance with an illustrative embodiment. In one embodiment, the communications environment 2400 may include an endoscopic peripheral 2402, an associated identification 2404, a laptop 2406, networks 2408, a content management system 2410, a server 2412, a database 2414, a computer 2416, and a display 2418.

The endoscopic peripheral 2402 may be configured to capture content that is subsequently streamed to a remote location whether it be the laptop 2406 or the display 2418. In one embodiment, the endoscopic peripheral 2402 may include the identifier 2404 for identifying content captured by the endoscopic peripheral 2402. The identifier 2404 may be a hardware or software identifier. For example, the identifier 2404 may be a MAC address, IP address, serial number, IMEI, or user assigned identifier, such as a name.

In one embodiment, the endoscopic peripheral 2402 includes a memory configured to store the identifier 2404. The endoscopic peripheral 2402 may be configured to be plug and play compatible. However, in other embodiments, the endoscopic peripheral 2402 may store scripts, updates, software, or a set of instructions and commands for utilizing and interfacing the endoscopic peripheral 2402. The endoscopic peripheral 2402 may also be configured to store captured image content. As a result, the content may be easily moved from one location to another and uploaded and communicated as needed. This may be particularly useful for remote settings, such as military operations, rural areas, triage areas, and so forth.

The laptop 2406 may utilize a default application or a specialized application to view the content captured or visualized by the endoscopic peripheral 2402. For example, any number of default video or content applications, operating systems, or so forth may be utilized to view, save, and manage the content.

The laptop 2406 or the endoscopic peripheral 2402 may communicate with the networks 2408. The laptop 2406 is representative of any number of computing or communications devices. The networks 2408 represent one or more communications networks as are herein described. The connections between the components may be wired or wireless.

Communications of content from the endoscopic peripheral 2402 may be communicated to the content management system 2410. The content management system 2410 may represent a cloud computing system, server farm, or other communications system. In one embodiment, the server 2412 may be accessed by the laptop 2406 to stream the captured content. The database 2414 may represent one or more databases storing the captured content. In one embodiment, the computer 2416 may access content captured by the endoscopic peripheral 2402 from the content management system 2410. In another embodiment, the computer 2416 may access the content from the laptop 2406 through the network. A user may utilize the computer 2416 and the display 2418 to view the content captured by the endoscopic peripheral 2402. For example, the user may be a doctor remotely located from the endoscopic peripheral 2402 that has been loaned to a rural patient. The content may be captured and communicated in real-time (or near/substantial real time) or as non-real time communications.

In one embodiment, the endoscopic peripheral 2402 or software stored in or associated with the endoscopic peripheral 2402 may be configured to automatically communicate with the content management system 2410 (or respective components) or the computer 2416. The communications may be routed utilizing a hardware address or software address, such as a MAC address, IP address, website, secured tunnel, or so forth.

The previous detailed description is of a small number of embodiments for implementing the invention and is not intended to be limiting in scope. The following claims set forth a number of the embodiments of the invention disclosed with greater particularity.

What is claimed:

1. An endoscopic peripheral, comprising:
   flexible cable a first end of the flexible cable, the first end including at least a camera and one or more lights enclosed by a tip at the first end, the tip is rounded for insertion of a portion of the first end into a body of a patient;
   a second end of the flexible cable terminating in a plug configured to physically connect the endoscopic peripheral to an electronic device including a display that is external to a body of a patient, the electronic device powers the camera and the one or more lights and displays content captured by the camera, wherein the endoscopic peripheral is plug-and-play when connected to the electronic device, wherein the plug-and-play complies with the Universal Plug and Play (UPnP) standard, and
   wherein a diameter of the endoscopic peripheral is constant from the tip of the first end to the plug of the second end.

2. The endoscopic peripheral of claim 1, wherein the camera captures high definition content.

3. The endoscopic peripheral of claim 2, wherein the high definition content is captured by default applications of the electronic device.

4. The endoscopic peripheral of claim 2, wherein the first end includes a flexible portion configured to bend from a first position into one or more bent positions under a minimal application of force.

5. The endoscopic peripheral of claim 1, wherein an angle of the camera and the one or more lights is adjustable.

6. The endoscopic peripheral of claim 1, further comprising:
   a memory connected to the camera, the memory is configured to store the content captured by the camera for subsequent access.

7. The endoscopic peripheral of claim 6, wherein the memory includes an application for interfacing the endoscopic peripheral with the electronic device.

8. The endoscopic peripheral of claim 1, further comprising:
   a disposable cover over the first end.

9. The endoscopic peripheral of claim 1, further comprising:
   shielding surrounding the camera, one or more lights, and wiring within the endoscopic peripheral.

10. The endoscopic peripheral of claim 1, wherein the first end is replaceable to replace the camera and the one or more lights.

11. The endoscopic peripheral of claim 1, wherein the plug is a miniatured plug for interfacing with the electronic device.

12. An endoscopic peripheral, comprising:
flexible cable a first end of the flexible cable, the first end including at least a camera and one or more lights enclosed by a tip at the first end, the tip is rounded for insertion of a portion of the first end into a body of a patient;
a second end of the flexible cable terminating in a plug configured to physically connect the endoscopic peripheral to a wireless device including a display that is external to a body of a patient, the wireless device powers the camera and the one or more lights and displays content captured by the camera, wherein the endoscopic peripheral is plug-and-play when connected to the electronic device, wherein the plug-and-play complies with the Universal Plug and Play (UPnP) standard, and
wherein a diameter of the endoscopic peripheral is constant from the tip of the first end to the plug of the second end.

13. The endoscopic peripheral of claim 12, wherein the tip is clear for capturing videos or images by the camera.

14. The endoscopic peripheral of claim 12, further comprising:
a memory connected to the camera, the memory is configured to store the content captured by the camera for subsequent access.

15. The endoscopic peripheral of claim 12, further comprising:
a latch configured to temporarily connect a disposable cover over the first end of the endoscopic peripheral.

16. The endoscopic peripheral of claim 12, wherein the first end is interchangeable to change the camera and the one or more lights utilized with the wireless endoscope.

17. The endoscopic peripheral of claim 12, further comprising:
logic for streaming the content through one or more communications networks to one or more remote addresses in response to an identifier associated with the endoscopic peripheral.

18. The endoscopic peripheral of claim 12, wherein the camera captures a plurality of spectra for examining the body of the patient.

19. The endoscopic peripheral of claim 12, wherein the first end includes a stopper for preventing over insertion of the first end in the body of the user.

20. The endoscopic peripheral of claim 12, further comprising:
a plurality of disposable covers utilized over all or a portion of the first end.

21. The endoscopic peripheral of claim 12, wherein the camera captures high definition content.

22. The endoscopic peripheral of claim 12, wherein the first end is replaceable to replace the camera and the one or more lights.

23. The endoscopic peripheral of claim 12, further comprising:
shielding surrounding the camera, one or more lights, and wiring within the endoscopic peripheral.

24. The endoscopic peripheral of claim 12, wherein the plug is a miniatured plug for interfacing with the electronic device.

* * * * *